(12) United States Patent
Levit

(10) Patent No.: US 11,498,975 B2
(45) Date of Patent: *Nov. 15, 2022

(54) TREATMENT OF DIABETES MELLITUS

(71) Applicant: Eyal Levit, Brooklyn, NY (US)

(72) Inventor: Eyal Levit, Brooklyn, NY (US)

(*) Notice: Subject to any disclaimer, the term of this patent is extended or adjusted under 35 U.S.C. 154(b) by 144 days.

This patent is subject to a terminal disclaimer.

(21) Appl. No.: 17/007,451

(22) Filed: Aug. 31, 2020

(65) Prior Publication Data

US 2020/0399388 A1 Dec. 24, 2020

Related U.S. Application Data

(63) Continuation of application No. 16/108,937, filed on Aug. 22, 2018, now Pat. No. 10,759,865.

(60) Provisional application No. 62/620,135, filed on Jan. 22, 2018, provisional application No. 62/548,541, filed on Aug. 22, 2017.

(51) Int. Cl.
| | | |
|---|---|---|
| *C07K 16/28* | (2006.01) | |
| *A61K 39/395* | (2006.01) | |
| *A61K 9/00* | (2006.01) | |
| *A61K 31/519* | (2006.01) | |
| *A61P 3/10* | (2006.01) | |
| *A61K 47/26* | (2006.01) | |
| *A61K 9/08* | (2006.01) | |
| *A61K 47/12* | (2006.01) | |
| *A61K 9/20* | (2006.01) | |
| *A61K 47/02* | (2006.01) | |
| *A61K 47/18* | (2017.01) | |
| *A61K 39/00* | (2006.01) | |

(52) U.S. Cl.
CPC ........ *C07K 16/2887* (2013.01); *A61K 9/0019* (2013.01); *A61K 9/0053* (2013.01); *A61K 9/08* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 31/519* (2013.01); *A61K 39/3955* (2013.01); *A61K 47/02* (2013.01); *A61K 47/12* (2013.01); *A61K 47/183* (2013.01); *A61K 47/26* (2013.01); *A61P 3/10* (2018.01); *A61K 9/20* (2013.01); *A61K 2039/505* (2013.01); *A61K 2039/54* (2013.01); *A61K 2039/545* (2013.01); *A61K 2039/55* (2013.01)

(58) Field of Classification Search
CPC .............. C07K 16/2887; A61K 9/0053; A61K 31/519; A61K 9/0019; A61K 9/08; A61K 47/12; A61K 9/2054; A61K 9/2009; A61K 9/2027; A61K 47/02; A61K 9/2031; A61K 9/2013; A61K 9/2018; A61K 47/183; A61K 39/3955; A61K 2039/505; A61K 9/20; A61P 3/10

See application file for complete search history.

(56) References Cited

U.S. PATENT DOCUMENTS 10,759,865 B2 * 9/2020 Levit ................. A61K 9/08

* cited by examiner

*Primary Examiner* — Shirley V Gembeh

(74) *Attorney, Agent, or Firm* — Kramer Levin Naftalis & Frankel LLP

(57) ABSTRACT

The present invention provides a method of treating insulin-dependent diabetes mellitus in a subject, comprising administering to the subject a therapeutically effective amount of a Janus kinase inhibitor, or a pharmaceutically acceptable salt or ester thereof, or a therapeutically effective amount of intravenous immunoglobulin, or a therapeutically effective amount of a therapeutic agent that destroys B lymphocytes, or a combination thereof. The present invention also provides kits containing the same.

15 Claims, No Drawings

TREATMENT OF DIABETES MELLITUS

CROSS-REFERENCE TO RELATED APPLICATIONS

This application is a continuation of U.S. patent application Ser. No. 16/108,937, filed on Aug. 22, 2018, which claims the benefit of U.S. Provisional Patent Application No. 62/548,541, filed on Aug. 22, 2017, and U.S. Provisional Patent Application No. 62/620,135, filed on Jan. 22, 2018, the contents of these applications are incorporated by reference in their entireties.

FIELD OF THE INVENTION

The invention relates to treatments of insulin-dependent diabetes mellitus (IDDM).

BACKGROUND OF THE INVENTION

Insulin-dependent diabetes mellitus (IDDM), also known as type I diabetes, is characterized by reduced insulin production and hyperglycemia, i.e., high blood glucose levels, which ultimately results in a variety of early symptoms in humans, including increased thirst, frequent urination, extreme hunger, unintended weight loss, fatigue and blurred vision. Untreated, IDDM can ultimately lead to tissue damage, resulting in increased risk of heart attacks and strokes, neuropathy, retinopathy, kidney failure and, ultimately, death. IDDM is one of the most prevalent metabolic disorders in the world. In the United States, approximately one in 300 to 400 people are affected by this disease. Some studies suggest that the incidence of IDDM in the United States is continuing to rise.

Different therapies have been employed for treating IDDM. By far the most commonly employed therapy for the clinical symptoms of IDDM is exogenous insulin replacement. However, while insulin replacement therapy allows most IDDM patients to lead somewhat normal lives, this therapy is imperfect and does not completely restore metabolic homeostasis. As a result, severe complications including dysfunctions of the eye, kidney, heart, and other organs are common in diabetic patients undergoing insulin replacement therapy. See U.S. Pat. No. 6,207,159, which is hereby incorporated by reference in its entirety.

Another common treatment for the clinical symptoms of IDDM is pancreatic or beta-islet cell transplantation. However, the insulin-producing beta-cells of transplanted tissues are often rapidly destroyed by the same autoimmune response which previously destroyed the patient's own pancreatic tissue. Therefore, the use of immune-suppressants after transplantation is common, carrying with it the adverse side effects described above. See U.S. Pat. No. 6,207,159, which is hereby incorporated by reference in its entirety.

There remains a need for improved treatments of IDDM. The present invention addresses this need.

SUMMARY OF THE INVENTION

The present invention provides a method of treating insulin-dependent diabetes mellitus in a subject, comprising administering to the subject a therapeutically effective amount of a Janus kinase inhibitor, or a pharmaceutically acceptable salt or ester thereof, or a therapeutically effective amount of intravenous immunoglobulin, or a therapeutically effective amount of a therapeutic agent that destroys B lymphocytes, or a combination thereof.

In some embodiments of the present invention, the method comprises administering to the subject a therapeutically effective amount of a Janus kinase inhibitor, or a pharmaceutically acceptable salt or ester thereof, and a therapeutically effective amount of intravenous immunoglobulin.

In some embodiments of the present invention, the method comprises administering to the subject a therapeutically effective amount of a Janus kinase inhibitor, or a pharmaceutically acceptable salt or ester thereof, and a therapeutically effective amount of a therapeutic agent that destroys B lymphocytes.

In some embodiments of the present invention, the method comprises administering to the subject a therapeutically effective amount of intravenous immunoglobulin and a therapeutically effective amount of a therapeutic agent that destroys B lymphocytes.

In some embodiments of the present invention, the method comprises administering a therapeutically effective amount of a Janus kinase inhibitor, or a pharmaceutically acceptable salt or ester thereof, and a therapeutically effective amount of intravenous immunoglobulin, and a therapeutically effective amount of a therapeutic agent that destroys B lymphocytes.

In some embodiments of the present invention, the Janus kinase inhibitor, or a pharmaceutically acceptable salt or ester thereof, is selected from the group consisting of a JAK1/3 inhibitor and a JAK3 inhibitor.

In some embodiments of the present invention, the Janus kinase inhibitor, or a pharmaceutically acceptable salt or ester thereof, is tofacitinib.

In some embodiments of the present invention, the Janus kinase inhibitor, or a pharmaceutically acceptable salt or ester thereof, is tofacitinib citrate.

In some embodiments of the present invention, the therapeutic agent that destroys B lymphocytes is a therapeutic agent that binds to B lymphocytes.

In some embodiments of the present invention, the therapeutic agent that destroys B lymphocytes is an antibody agent.

In some embodiments of the present invention, the antibody agent is an anti-CD20 antibody agent.

In some embodiments of the present invention, the anti-CD20 antibody agent is associated with a payload entity.

In some embodiments of the present invention, the payload entity is a therapeutic agent.

In some embodiments of the present invention, the anti-CD20 antibody agent is an antibody or fragment thereof.

In some embodiments of the present invention, the anti-CD20 antibody agent comprises amino acid sequences substantially identical to the CDRs of rituximab.

In some embodiments of the present invention, the anti-CD20 antibody agent is rituximab or a fragment thereof.

In some embodiments of the present invention, the anti-CD20 antibody agent is rituximab.

In some embodiments of the present invention, the Janus kinase inhibitor, or a pharmaceutically acceptable salt or ester thereof, is tofacitinib citrate and the therapeutic agent that destroys B lymphocytes is rituximab.

In some embodiments of the present invention, the subject has been diagnosed with a viral infection.

In some embodiments of the present invention, the viral infection is caused by infection with Coxsackievirus.

In some embodiments of the present invention, tofacitinib citrate is administered orally.

In some embodiments of the present invention, tofacitinib citrate is administered as a tablet.

In some embodiments of the present invention, the tablet is an immediate-release tablet, comprising one or more binders, or one or more diluents, or one or more disintegrants, or one or more lubricants, or combinations thereof.

In some embodiments of the present invention, the immediate-release tablet comprises tofacitinib citrate and the excipients microcrystalline cellulose, lactose monohydrate, croscarmellose sodium, magnesium stearate, HPMC 2910/Hypromellose 6 cP, titanium dioxide, macrogol/PEG3350, and triacetin.

In some embodiments of the present invention, the immediate-release tablet comprises about 8 mg tofacitinib citrate.

In some embodiments of the present invention, the immediate-release tablet comprises 8 mg tofacitinib citrate.

In some embodiments of the present invention, the tablet is an extended-release tablet, comprising one or more binders, or one or more diluents, or one or more disintegrants, or one or more lubricants, or combinations thereof.

In some embodiments of the present invention, the extended-release tablet comprises tofacitinib citrate and the excipients sorbitol, hydroxyethyl cellulose, copovidone, magnesium stearate, cellulose acetate, hydroxypropyl cellulose, HPMC 2910/Hypromellose, titanium dioxide, triacetin, and red iron oxide.

In some embodiments of the present invention, the extended-release tablet comprises about 17.77 mg tofacitinib citrate.

In some embodiments of the present invention, the extended-release tablet comprises 17.77 mg tofacitinib citrate.

In some embodiments of the present invention, the intravenous immunoglobulin is administered as a sterile solution for injection comprising from 9%-11% protein in 0.16-0.24 M glycine.

In some embodiments of the present invention, rituximab is administered intravenously.

In some embodiments of the present invention, rituximab to be administered is formulated in polysorbate 80 (0.7 mg/mL), sodium chloride (9 mg/mL), sodium citrate dihydrate (7.35 mg/mL), and water, at a pH of 6.5.

In some embodiments of the present invention, rituximab to be administered is formulated at a concentration of 10 mg/ml.

In some embodiments of the present invention, rituximab to be administered is diluted to a final concentration of 1 mg/mL to 4 mg/mL in an infusion bag containing either 0.9% Sodium Chloride, USP, or 5% Dextrose in Water, USP, before administration.

In some embodiments of the present invention, tofacitinib citrate is administered at a dose of 8 or 16 mg twice daily.

In some embodiments of the present invention, the intravenous immunoglobulin is administered at a dose of 1 to 2 mg per kg weight of the subject every 1 to 3 weeks.

In some embodiments of the present invention, the intravenous immunoglobulin is administered at a dose of 2 mg per kg weight of the subject on the first day of treatment followed by doses of 1 mg per kg weight of the subject on the second and third days, and wherein the intravenous immunoglobulin is administered at a dose of 1 to 2 mg per kg weight of the subject every 1 to 3 weeks thereafter.

In some embodiments of the present invention, rituximab is administered at a dose of 375 mg/m2 surface of the subject once per week.

In some embodiments of the present invention, rituximab is administered at a dose of 375 mg/m2 surface of the subject once per week for a period of three weeks.

The present invention provides a method of treating insulin-dependent diabetes mellitus in a subject, comprising administering to the subject twice daily two immediate-release tablets each comprising 8 mg of tofacitinib citrate and the excipients microcrystalline cellulose, lactose monohydrate, croscarmellose sodium, magnesium stearate, HPMC 2910/Hypromellose 6 cP, titanium dioxide, macrogol/PEG3350, and triacetin, and administering to the subject 1 to 2 mg intravenous immunoglobulin per kg weight of subject every 1 to 3 weeks.

The present invention provides a method of treating insulin-dependent diabetes mellitus in a subject, comprising administering to the subject twice daily two immediate-release tablets each comprising 8 mg of tofacitinib citrate; administering to the subject intravenous immunoglobulin at a dose of 2 mg per kg weight of the subject on the first day of treatment followed by doses of 1 mg per kg weight of the subject on the second and third days, and wherein the intravenous immunoglobulin is administered at a dose of 1 mg per kg weight of the subject every 3 weeks thereafter for a total of 5 to 6 months; and administering to the subject rituximab at a dose of 375 mg/m2 surface of the subject once per week for a period of three weeks.

The present invention provides a kit for the treatment of insulin-dependent diabetes mellitus in a subject, comprising a Janus kinase inhibitor, or a pharmaceutically acceptable salt or ester thereof, and intravenous immunoglobulin.

The present invention provides a kit for the treatment of insulin-dependent diabetes mellitus in a subject, comprising a Janus kinase inhibitor, or a pharmaceutically acceptable salt or ester thereof, and a therapeutic agent that destroys B lymphocytes.

The present invention provides a kit for the treatment of insulin-dependent diabetes mellitus in a subject, comprising a Janus kinase inhibitor, or a pharmaceutically acceptable salt or ester thereof, and intravenous immunoglobulin, and a therapeutic agent that destroys B lymphocytes.

In some embodiments of the present kit invention, the Janus kinase inhibitor, or a pharmaceutically acceptable salt or ester thereof, is tofacitinib citrate; and wherein the therapeutic agent that destroys B lymphocytes is rituximab.

The present invention provides a kit for the treatment of insulin-dependent diabetes mellitus in a subject, comprising intravenous immunoglobulin and a therapeutic agent that destroys B lymphocytes.

The present invention provides a method of treating insulin-dependent diabetes mellitus in a subject, comprising administering to the subject tofacitinib citrate; and administering to the subject intravenous immunoglobulin; and administering to the subject rituximab.

In some embodiments of the present invention, the tofacitinib citrate is administered at a dose from 4 mg to 64 mg per day; and wherein the intravenous immunoglobulin is administered at a dose of from 0.2 mg to 100 mg per kg weight of the subject every 1 to 4 weeks; and wherein the rituximab is administered at a dose of from 50 mg/m2 to 700 mg/m2 surface of the subject every 1 to 4 weeks.

In some embodiments of the present invention, the tofacitinib citrate is administered as immediate-release tablet or extended-release tablet comprising from 2 mg to 30 mg tofacitinib citrate; and wherein the intravenous immunoglobulin is administered as a sterile solution for injection comprising from 2%-50% protein; and wherein the rituximab is administered intravenously at a concentration of 0.2 mg/mL to 20 mg/mL.

In some embodiments of the present invention, the tofacitinib citrate is administered at a dose from about 8 mg to about 32 mg per day as an immediate-release tablet comprising about 8 mg tofacitinib citrate or as an extended-release tablet comprising about 17.77 mg tofacitinib citrate or both; and wherein the intravenous immunoglobulin is administered as a sterile solution for injection comprising from 5%-20% protein at a dose of from 1 mg to 2 mg per kg weight of the subject every 1 to 4 weeks; and wherein the rituximab is administered intravenously at a concentration of 1 mg/mL to 4 mg/mL at a dose of 375 mg/m2 surface of the subject once per week.

In some embodiments of the present invention, the tofacitinib citrate is administered at a dose of 32 mg per day as an immediate-release tablet comprising about 8 mg tofacitinib citrate; and wherein the intravenous immunoglobulin is administered at a dose of 1 mg per kg weight of the subject every 3 weeks for a total of 5 to 6 months, and wherein intravenous immunoglobulin is administered at a dose of 2 mg per kg weight of the subject on a first day of treatment followed by doses of 1 mg per kg weight of the subject on second and third days of treatment; and wherein the rituximab is administered for a period of three weeks.

The present invention provides a method of treating insulin-dependent diabetes mellitus in a subject, comprising administering to the subject tofacitinib citrate; and administering to the subject intravenous immunoglobulin.

In some embodiments of the present invention, the tofacitinib citrate is administered at a dose from 4 mg to 64 mg per day; and wherein the intravenous immunoglobulin is administered at a dose of from 0.2 mg to 100 mg per kg weight of the subject every 1 to 4 weeks.

In some embodiments of the present invention, the tofacitinib citrate is administered as immediate-release tablet or extended-release tablet comprising from 2 mg to 30 mg tofacitinib citrate; and wherein the intravenous immunoglobulin is administered as a sterile solution for injection comprising from 2%-50% protein.

In some embodiments of the present invention, the tofacitinib citrate is administered at a dose from about 8 mg to about 32 mg per day as an immediate-release tablet comprising about 8 mg tofacitinib citrate or as an extended-release tablet comprising about 17.77 mg tofacitinib citrate or both; and wherein the intravenous immunoglobulin is administered as a sterile solution for injection comprising from 5%-20% protein at a dose of from 1 mg to 2 mg per kg weight of the subject every 1 to 4 weeks.

In some embodiments of the present invention, the tofacitinib citrate is administered at a dose of 32 mg per day as an immediate-release tablet comprising about 8 mg tofacitinib citrate; and wherein the intravenous immunoglobulin is administered at a dose of 1 mg per kg weight of the subject every 3 weeks for a total of 5 to 6 months, and wherein intravenous immunoglobulin is administered at a dose of 2 mg per kg weight of the subject on a first day of treatment followed by doses of 1 mg per kg weight of the subject on second and third days of treatment.

In some embodiments of the present invention, therapeutically effective amounts of tofacitinib citrate, and intravenous immunoglobulin, and rituximab are administered.

In some embodiments of the present invention, therapeutically effective amounts of tofacitinib citrate and intravenous immunoglobulin, are administered.

In some embodiments of the present invention, the subject is in need of treatment.

The present invention provides a therapeutically effective amount of a Janus kinase inhibitor, or a pharmaceutically acceptable salt or ester thereof, or a therapeutically effective amount of intravenous immunoglobulin, or a therapeutically effective amount of a therapeutic agent that destroys B lymphocytes, or a combination thereof, for use in the treatment of insulin-dependent diabetes mellitus in a subject.

The present invention provides for the use of a therapeutically effective amount of a Janus kinase inhibitor, or a pharmaceutically acceptable salt or ester thereof, or a therapeutically effective amount of intravenous immunoglobulin, or a therapeutically effective amount of a therapeutic agent that destroys B lymphocytes, or a combination thereof, for the manufacture of a medicament for the treatment of insulin-dependent diabetes mellitus in a subject.

The present invention provides tofacitinib and intravenous immunoglobulin for use in the treatment of insulin-dependent diabetes mellitus in a subject, wherein two immediate-release tablets each comprising 8 mg of tofacitinib citrate and the excipients microcrystalline cellulose, lactose monohydrate, croscarmellose sodium, magnesium stearate, HPMC 2910/Hypromellose 6 cP, titanium dioxide, macrogol/PEG3350, and triacetin are administered to the subject twice daily; and wherein 1 to 2 mg intravenous immunoglobulin per kg weight of the subject is administered to the subject every 1 to 3 weeks.

The present invention provides tofacitinib and intravenous immunoglobulin and rituximab for use in the treatment of insulin-dependent diabetes mellitus in a subject, wherein two immediate-release tablets each comprising 8 mg of tofacitinib citrate are administered to the subject twice daily; wherein intravenous immunoglobulin is administered to the subject at a dose of 2 mg per kg weight of the subject on the first day of treatment followed by doses of 1 mg per kg weight of the subject on the second and third days, and wherein the intravenous immunoglobulin is administered at a dose of 1 mg per kg weight of the subject every 3 weeks thereafter for a total of 5 to 6 months; and wherein rituximab is administered to the subject at a dose of 375 mg/m$^2$ surface of the subject once per week for a period of three weeks.

The present invention provides the use of tofacitinib and intravenous immunoglobulin for the manufacture of a medicament for the treatment of insulin-dependent diabetes mellitus in a subject, wherein two immediate-release tablets each comprising 8 mg of tofacitinib citrate and the excipients microcrystalline cellulose, lactose monohydrate, croscarmellose sodium, magnesium stearate, HPMC 2910/Hypromellose 6 cP, titanium dioxide, macrogol/PEG3350, and triacetin are administered to the subject twice daily; and wherein 1 to 2 mg intravenous immunoglobulin per kg weight of the subject is administered to the subject every 1 to 3 weeks.

The present invention provides the use of tofacitinib and intravenous immunoglobulin and rituximab for the manufacture of a medicament for the treatment of insulin-dependent diabetes mellitus in a subject, wherein two immediate-release tablets each comprising 8 mg of tofacitinib citrate are administered to the subject twice daily; wherein intravenous immunoglobulin is administered to the subject at a dose of 2 mg per kg weight of the subject on the first day of treatment followed by doses of 1 mg per kg weight of the subject on the second and third days, and wherein the intravenous immunoglobulin is administered at a dose of 1 mg per kg weight of the subject every 3 weeks thereafter for a total of 5 to 6 months; and wherein rituximab is administered to the subject at a dose of 375 mg/m² surface of the subject once per week for a period of three weeks.

In some embodiments of the present invention, the use is as in any of the embodiments of the present invention set forth herein.

DETAILED DESCRIPTION OF THE INVENTION

Terms used herein shall be accorded the following defined meanings, unless otherwise indicated elsewhere herein.

The term "a" should be understood to mean "at least one"; and the terms "about" and "approximately" should be understood to permit standard variation as would be understood by those of ordinary skill in the art; and where ranges are provided, endpoints are included.

Administration: As used herein, the term "administration" or "administering" refers to the administration of a compound, composition, dosage form and the like to a patient, subject or system. Administration to a subject (e.g., to a human) may be facilitated by any appropriate route. For example, in some embodiments of the present invention, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or intravitreal. In some embodiments of the present invention, administration may involve intermittent dosing. In some embodiments of the present invention, administration may involve continuous dosing (e.g., perfusion) for at least a selected period of time.

Affinity: As is known in the art, "affinity" is a measure of the tightness with which a particular ligand binds to its binding partner, for example a receptor. Affinities can be measured in various ways generally known to the person having ordinary skill in the art. In some embodiments of the present invention, affinity is measured by a quantitative assay. In some such embodiments, binding partner concentration may be fixed to be in excess of ligand concentration so as to mimic physiological conditions. Alternatively or additionally, in some embodiments of the present invention, binding partner concentration and/or ligand concentration may be varied. In some such embodiments, affinity may be compared to a reference under comparable conditions (e.g., concentrations).

Agent: The term "agent" as used herein may refer to a compound or entity of any chemical class including, for example, small molecules, polypeptides, nucleic acids, saccharides, lipids, metals, or combinations thereof. As will be clear from context, in some embodiments, an agent can be or comprise a cell or organism, or a fraction, extract, or component thereof. In some embodiments of the present invention, an agent is or comprises a natural product in that it is found in and/or is obtained from nature. In some embodiments of the present invention, an agent is or comprises one or more entities that is man-made in that it is designed, engineered, and/or produced through action of the hand of man and/or is not found in nature. In some embodiments of the present invention, an agent may be utilized in isolated or pure form; in some embodiments of the present invention, an agent may be utilized in crude form. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc.

Animal: As used herein, the term "animal" refers to any member of the animal kingdom, including humans.

Antibody: As used herein, the term "antibody" refers to a polypeptide that includes canonical immunoglobulin sequence elements sufficient to confer specific binding to a particular target antigen. As is known in the art, intact antibodies as produced in nature are typically approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies may also be glycosylated, typically on the CH2 domain. Each variable domain contains three hypervariable loops known as complement determining regions (CDR1, CDR2, and CDR3) and four somewhat invariant framework regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen-binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (a1, a2, $\gamma^1$, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments of the present invention, an antibody is polyclonal; in some embodiments of the present invention, an antibody is monoclonal. In some embodiments of the present invention, an antibody has constant region sequences that are characteristic of mouse, rabbit, primate, or human antibodies. In some embodiments of the present invention, antibody sequence elements are humanized, primatized, chimeric, etc., as is known in the art. Moreover, the term antibody as used herein, will be understood to refer in appropriate embodiments (unless otherwise stated or clear from context) to any of the art-known or developed constructs or formats for capturing antibody structural and functional features in alternative presentation. In some embodiments of the present invention, an antibody may lack a covalent modification (e.g., attachment of a glycan) that it would have if produced naturally. In some embodiments of the present invention, an antibody may contain a covalent modification (e.g., attachment of a glycan, a payload [e.g., a detectable moiety, a therapeutic moiety, a catalytic moiety, etc.]), or other pendant group (e.g., poly-ethylene glycol, etc.). As used herein, the term antibody includes antibody fragments, such as, but not limited to, Fc and Fab fragments.

Antibody agent: As used herein, the term "antibody agent" refers to an agent that binds to one or more antigens. In some embodiments of the present invention, the term encompasses any polypeptide with immunoglobulin structural elements sufficient to confer specific binding, such as, but not limited to, antibodies and antibody fragments. Suitable antibody agents include, but are not limited to, human antibodies, humanized antibodies, primatized antibodies, mouse antibodies, rabbit antibodies, rat antibodies, sheep antibodies, donkey antibodies, horse antibodies, chimeric antibodies, bi-specific antibodies, conjugated antibodies (i.e., antibodies conjugated or fused to other proteins, radiolabels, cytotoxins), Small Modular ImmunoPharmaceuticals ("SMIPs™"), single chain antibodies (scAbs), cameloid antibodies, and antibody fragments. As used herein, the term antibody agent also includes intact monoclonal antibodies, polyclonal antibodies, single domain antibodies (e.g., shark single domain antibodies (e.g., IgNAR or fragments thereof)), multispecific antibodies (e.g. bi-specific antibodies, zybodies, etc.) formed from at least two intact antibodies, and antibody fragments so long as they exhibit the desired biological activity. In some embodiments of the present invention, the term antibody agent encompasses stapled peptides. In some embodiments of the present invention, the term antibody agent encompasses one or more antibody-like binding peptidomimetics. In some embodiments of the present invention, the term encompasses one or more antibody-like binding scaffold proteins. In come embodiments, the term encompasses monobodies or adnectins. In some embodiments of the present invention, an antibody agent is or comprises a polypeptide whose amino acid sequence includes one or more structural elements recognized by those skilled in the art as a complementarity determining region (CDR). In some embodiments of the present invention, an antibody agent is or comprises a polypeptide whose amino acid sequence includes at least one CDR (e.g., at least one heavy chain CDR and/or at least one light chain CDR) that is substantially identical to one found in a reference antibody. In some embodiments of the present invention, an included CDR is substantially identical to a reference CDR in that it is either identical in sequence or contains between 1-5 amino acid substitutions as compared with the reference CDR. In some embodiments of the present invention an included CDR is substantially identical to a reference CDR in that it shows at least 85%, 86%, 87%, 88%, 89%, 90%, 91%, 92%, 93%, 94%, 95%, 96%, 97%, 98%, 99%, or 100% amino acid sequence identity with the reference CDR. In some embodiments of the present invention, an antibody agent is or comprises a polypeptide whose amino acid sequence includes structural elements recognized by those skilled in the art as an immunoglobulin variable domain. In some embodiments of the present invention, an antibody agent is a polypeptide protein having a binding domain which is homologous or largely homologous to an immunoglobulin-binding domain. The term antibody agent includes chimeric antigen receptors. An anti-CD20 antibody agent is an antibody agent that specifically binds to the CD20 antigen.

Antibody fragment: As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some embodiments of the present invention, an antibody fragment contains sufficient amino acid sequence of the parent antibody of which it is a fragment that it binds to the same antigen as does the parent antibody; in some embodiments of the present invention, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids Antigen: An "antigen" is a molecule or entity that (i) elicits an immune response; and/or (ii) is specifically bound by a T cell receptor (e.g., when presented by an MHC molecule) or an antibody (e.g., produced by a B cell), for example when exposed or administered to an organism. In some embodiments of the present invention, an antigen elicits a humoral response (e.g., including production of antigen-specific antibodies) in an organism; alternatively or additionally, in some embodiments of the present invention, an antigen elicits a cellular response (e.g., involving T-cells whose receptors specifically interact with the antigen) in an organism.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

CD20: The term "CD20" or "CD20 antigen", as used herein, refers to the CD20 antigen, which is expressed for example on the surface B-lymphocytes.

Combination therapy: The term "combination therapy", as used herein, refers to those situations in which two or more different therapeutic agents are administered in combination with each other, i.e., in overlapping or sequential regimens so that the subject is simultaneously or sequentially exposed to the two or more therapeutic agents. When one therapeutic agent is administered "in combination with" one or more other therapeutic agents, it is not intended to imply that the therapeutic agents must be administered at the same time and/or formulated for delivery together in one dosage unit, although these methods of delivery are within the scope of the invention. Compositions containing a therapeutic agent can be administered concurrently with, prior to, or subsequent to, one or more other compositions containing a different therapeutic agent. In general, each therapeutic agent will be administered at a dose and/or on a time schedule determined to be optimal for that agent.

Dosage unit: As used herein, the term "dosage unit" refers to a physically discrete unit of one or more active pharmaceutical ingredients (e.g., a therapeutic or diagnostic or both) for administration to a subject. Each dosage unit contains a predetermined quantity of one or more active pharmaceutical ingredients. In some embodiments of the present invention, such quantity is a dose amount (or a whole fraction thereof) appropriate for administration in accordance with a dosing regimen that has been determined to correlate with a desired or beneficial outcome when administered to a relevant population. Those of ordinary skill in the art appreciate that the total amount of a therapeutic agent administered to a particular subject is determined by one or more attending physicians and may involve administration of multiple dosage units.

Dosage form: As used herein, the term "dosage form" refers to the type of a dosage unit, non-limiting examples of which are tablets, capsules, pills, solutions, suspensions, emulsion, powders, sustained-release formulations and the like.

Dosing regimen: As used herein, the term "dosing regimen" refers to a set of doses (typically more than one) that are administered individually to a subject, typically separated by periods of time. In some embodiments of the present invention, a given therapeutic agent has a recommended dosing regimen, which may involve one or more doses. In some embodiments of the present invention, a dosing regimen comprises a plurality of doses each of which are separated from one another by a time period of the same length; in some embodiments of the present invention, a dosing regimen comprises a plurality of doses and at least two different time periods separating individual doses. In some embodiments of the present invention, all doses within a dosing regimen have the same amount of therapeutic agent (i.e., the same dose amount). In some embodiments of the present invention, different doses within a dosing regimen have different amounts of therapeutic agent (i.e., different dose amounts). In some embodiments of the present invention, a dosing regimen comprises a first dose in a first dose amount, followed by one or more additional doses in a second dose amount different from the first dose amount. In some embodiments of the present invention, a dosing regimen comprises a first dose in a first dose amount, followed by one or more additional doses in a second dose amount that is the same as the first dose amount. In some embodiments of the present invention, a dosing regimen is correlated with a desired or beneficial outcome when administered across a relevant population (i.e., is a therapeutic dosing regimen).

Human: In some embodiments of the present invention, a human is an embryo, a fetus, an infant, a child, a teenager, or an adult.

Intravenous immunoglobulin: As used herein, the term "intravenous immunoglobulin" (also known as immunoglobulin therapy, normal human immunoglobulin, NHIG and IVIG) refers to a preparation of pooled immunoglobulins from the plasma of a plurality of blood donors for intravenous administration. In some embodiments of the present invention, the intravenous immunoglobulin comprises primarily IgG.

Janus kinase inhibitor: As used herein, the term "Janus kinase inhibitor" or "JAK inhibitor" refers to any agent (for example a small molecule compound) that interacts with and thereby reduces the signaling activity of a Janus kinase (JAK), preferably by reducing its enzymatic activity. It is thought that Janus kinase 3 (JAK3) primarily signals in combination with Janus kinase 1 (JAK1) in living cells. As used herein, the term "JAK1/3 inhibitor" refers to a Janus kinase inhibitor that reduces the signaling activity of the pair of JAK1 and JAK3 in living cells. As used herein, the term "JAK3 inhibitor" refers to Janus kinase inhibitor that reduces the signaling activity of JAK3. In some embodiments of the present invention, such reduction of signaling activity is at least about 50%, at least about 60%, at least about 75%, at least about 90%, at least about 95%, or at least about 99%. In some embodiments of the present invention, the concentration of a JAK inhibitor required to reduce the signaling activity of a JAK is less than about 1 μM, less than about 500 nM, less than about 100 nM, less than about 50 nM, less than about 10 nM, or less than about 1 nM. Preferably, the concentration of a JAK1/3 inhibitor that is required to reduce the signaling activity of the pair of JAK1 and JAK3 in living cells is lower than the concentration of the JAK1/3 inhibitor that is required to reduce the signaling activity of other pairs of JAKs in living cells to a comparable extent; in some embodiments of the present invention, this concentration is at least about 2-fold, at least about 5-fold, at least about 10-fold, at least about 20-fold, at least about 50-fold, at least about 100-fold, at least about 500-fold, or at least about 1000-fold lower. Preferably, the concentration of the JAK3 inhibitor that is required to reduce the signaling activity of JAK3 is lower than the concentration of the JAK3 inhibitor that is required to reduce the signaling activity of other JAKs to a comparable extent; in some embodiments of the present invention, this concentration is at least about 2-fold, at least about 5-fold, at least about 10-fold, at least about 20-fold, at least about 50-fold, at least about 100-fold, at least about 500-fold, or at least about 1000-fold lower. In some embodiments of the present invention, the extent by which a JAK inhibitor reduces the signaling activity of a JAK is expressed as the concentration of the JAK inhibitor needed to reduce the signaling activity of the JAK by 50%, also expressed as $IC_{50}$ (nM). Methods to measure the reduction of signaling activity of a Janus kinase (JAK), or of a pair of Janus kinases (JAKs) due to the presence of an inhibiter are generally known in the art and thus not provided in detail herein. Non-limiting examples of such methods are in vitro kinase assays and in vitro whole blood STAT phosphorylation assays, as described, e.g., in Meyer et al., Journal of Inflammation 7:41 (2010).

Patient: As used herein, the term "patient" refers to any animal (e.g., mammals such as mice, rats, rabbits, non-human primates, and/or humans) to which a composition, dosage unit or the like provided herein is or may be administered, e.g., for experimental, diagnostic, prophylactic, cosmetic, and/or therapeutic purposes. In some embodiments of the present invention, a patient is a human. In some embodiments of the present invention, a patient is suffering from or susceptible to one or more disorders or conditions. In some embodiments of the present invention, a patient displays one or more symptoms of a disorder or condition. In some embodiments of the present invention, a patient has been diagnosed with one or more disorders or conditions. In some embodiments of the present invention, the disorder or condition is or includes insulin dependent diabetes mellitus. As used herein, the nouns patient and subject have the same meaning and are used interchangeably.

Pharmaceutical composition: As used herein, the term "pharmaceutical composition" refers to a therapeutic agent that is formulated together with one or more pharmaceutically acceptable carriers. In some embodiments of the present invention, the therapeutic agent is present in a unit dose amount appropriate for administration in a therapeutic regimen. In some embodiments of the present invention, pharmaceutical compositions may be specially formulated for administration in solid or liquid form, including those adapted for the following: oral administration (for example in the form of tablets (e.g., those targeted for buccal, sublingual, and systemic absorption), boluses, powders, granules, pastes for application to the tongue); parenteral administration (for example in the form of subcutaneous, intramuscular, intravenous or epidural injections that may be sterile solutions or suspensions, or sustained-release formulations); topical administration (for example in the form of a cream, ointment, or a controlled-release patch or spray applied to the skin or oral cavity); intravaginal or intrarectal administration (for example in the form of a pessary, cream, or foam); sublingual administration; ocular administration; transdermal administration; nasal administration; pulmonary administration; or administration to other mucosal surfaces. As used herein, the terms carrier and excipient have the same meaning and are used interchangeably.

Therapeutic agent: As used herein, the term "therapeutic agent" in general refers to any agent that is administered for the purpose of treating a subject and that may elicit a desired response when administered to a subject. The terms therapeutic agent, active agent, active ingredient, active pharmaceutical ingredient and drug have the same meaning and are used interchangeably herein. Therapeutic agents include but are not limited to Janus kinase inhibitors, intravenous immunoglobulin and therapeutic agents that destroy B lymphocytes.

Therapeutic agent that destroys B lymphocytes: As used herein, the term "therapeutic agent that destroys B lymphocytes" refers to any therapeutic agent that, upon administration to a subject, directly or indirectly causes the death or destruction of at least some of the subject's B lymphocytes. In some embodiments of the present invention, at least about 10, 20, 30, 40, 50, 60, 70, 80 or 90% of the subject's B lymphocytes are destroyed, as determined by standard methods known to the person having ordinary skill in the art. The terms B lymphocytes and B cells are used interchangeably herein.

Therapeutic regimen: A "therapeutic regimen", as that term is used herein, refers to a dosing regimen, or a plurality of dosing regimens, administered to a subject for the purpose of treatment. A therapeutic regimen may comprise the administration of one or more therapeutic agents.

Therapeutically effective amount: As used herein, and unless otherwise specified herein, a "therapeutically effective amount" of a therapeutic agent is an amount that is sufficient, either by itself or in combination with one or more other therapeutic agents, to partially or completely alleviate, ameliorate, relive, inhibit, delay onset of, reduce severity of, and/or reduce incidence of one or more symptoms, features, and/or causes of a particular disease, disorder, and/or condition, or to partially or completely prevent any of the aforesaid from worsening. One or more of the aforesaid effects of a therapeutic agent regarding a disease, disorder, and/or condition may be measured, for example, on the clinical, tissue, cellular and/or molecular level. A person skilled in the art would recognize that the therapeutically effective amount, or dose, of the therapeutic agents disclosed herein can be determined based on the disclosures in this patent application (e.g., the Examples (IDDM biomarkers)) and common knowledge in the art. The term therapeutically effective amount does not require successful treatment or complete cure. Rather, a therapeutically effective amount may be an amount that provides only for a partial treatment or cure. The term therapeutically effective amount does not require that a therapeutic benefit is achieved in a particular subject. Rather, a therapeutically effective amount may achieve a therapeutic benefit only in number of subjects in need of treatment, but not all. In some embodiments of the present invention, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments of the present invention, a therapeutically effective amount may be formulated and/or administered in a single dosage unit and dose, respectively. In some embodiments of the present invention, a therapeutically effective amount may be formulated and/or administered in a plurality of dosage units and doses, respectively, for example, as part of a dosing regimen.

Tofacitinib: As used herein, the term tofacitinib refers to tofacitinib free base as well as any pharmaceutically acceptable salt thereof (e.g., citrate salt).

Treatment: As used herein, the term "treatment" (also "treat" or "treating") refers to any therapeutic or prophylactic/preventative measures the purpose of which is to partially or completely alleviate, ameliorate, relive, inhibit, delay onset of, reduce severity of, and/or reduce incidence of one or more symptoms, features, and/or causes of a particular disease, disorder, and/or condition, or to partially or completely prevent any of the aforesaid from worsening. In some embodiments of the present invention, treatment may be administered to a subject who does not exhibit signs of the relevant disease, disorder and/or condition and/or to a subject who exhibits only early signs of the disease, disorder, and/or condition. Alternatively or additionally, in some embodiments of the present invention, treatment may be administered to a subject who exhibits one or more established signs of the relevant disease, disorder and/or condition. In some embodiments of the present invention, a subject may be treated who has been diagnosed as suffering from the relevant disease, disorder, and/or condition. In some embodiments of the present invention, a subject may be treated that is known to have one or more susceptibility factors that are statistically correlated with increased risk of development of the relevant disease, disorder, and/or condition. Treatment may comprise the administration of one or more therapeutic agents to a subject. In some embodiments of the present invention, the term treatment (also "treat" or "treating") includes actually achieving to partially or completely alleviate, ameliorate, relive, inhibit, delay onset of, reduce severity of, and/or reduce incidence of one or more symptoms, features, and/or causes of a particular disease, disorder, and/or condition, or to partially or completely prevent any of the aforesaid from worsening. A person having ordinary skill in the art would know how to determine whether treatment (as defined herein) has occurred based on the disclosures in this specification and common knowledge in the art.

Insulin-Dependent Diabetes Mellitus (IDDM)

Insulin-dependent diabetes mellitus (IDDM) is characterized by reduced insulin production and hyperglycemia, i.e., high blood glucose levels. The root cause of IDDM is unknown. However, studies suggest that IDDM is caused, at least in part, by a T lymphocyte-mediated autoimmune response that leads to the destruction of insulin-producing pancreatic beta-cells. The commonly employed regimens for the treatment of insulin-dependent diabetes mellitus (IDDM) are primarily directed to alleviating the symptoms of the disease, and associated with sometimes severe complications and side effects.

The present invention is, in part, based on the recognition that IDDM can be treated in a subject by administration of a Janus kinase (JAK) inhibitor, intravenous immunoglobulin (IVIG) or a therapeutic agent that destroys B lymphocytes (B cells), or by various combinations thereof.

The present invention provides a method of treating insulin-dependent diabetes mellitus in a subject including administering to the subject a therapeutically effective amount of a Janus kinase inhibitor, or a pharmaceutically acceptable salt or ester thereof, therapeutically effective amount of intravenous immunoglobulin, or therapeutically effective amount of a therapeutic agent that destroys B lymphocytes, or combinations thereof.

In some embodiments of the present invention, the Janus kinase inhibitor, or a pharmaceutically acceptable salt or ester thereof, is a JAK1/3 inhibitor or JAK3 inhibitor.

In some embodiments of the present invention, the Janus kinase inhibitor, or a pharmaceutically acceptable salt or ester thereof, is a JAK1/3 inhibitor.

In some embodiments of the present invention, the Janus kinase inhibitor, or a pharmaceutically acceptable salt or ester thereof, is tofacitinib.

In a preferred embodiment of the present invention, the Janus kinase inhibitor, or a pharmaceutically acceptable salt thereof, is tofacitinib citrate.

In a preferred embodiment of the present invention, the therapeutic agent that destroys B lymphocytes (B cells) is the antibody rituximab.

JAK-STAT Pathway

Without wishing to be bound by any particular theory, the JAK-STAT pathway is believed to be a signal transduction cascade ubiquitous amongst vertebrates. It operates also in some, but not all, invertebrate organisms, for example *Drosophila melanogaster*. This pathway transmits information from the extracellular milieu to the cell nucleus, thereby regulating gene expression. JAK-STAT pathway activation stimulates a number of different basic cellular processes, including cell proliferation, differentiation, migration and apoptosis. These cellular events are critical to a number of different biological processes, including hematopoiesis, immune development, mammary gland development and lactation, adipogenesis, sexually dimorphic growth and other processes. JAK-STAT signaling has been implicated in the mediation of many abnormal immune responses such as allergies, asthma, autoimmune diseases such as transplant rejection, rheumatoid arthritis, amyotrophic lateral sclerosis and multiple sclerosis, as well as in solid and hematologic malignancies such as leukemias and lymphomas. See, e.g., Rawlins et al., Journal of Cell Science 117:1281-1283 (2004), and references cited therein.

The JAK-STAT pathway has basically three components, a transmembrane receptor, a Janus kinase (JAK) and two Signal Transducer and Activator of Transcription (STAT) proteins. According to the current model of JAK-STAT signaling, engagement of the transmembrane receptor with an extracellular ligand activates JAK proteins associated with the receptor's cytoplasmic domain. These activated JAK proteins then phosphorylate the cytoplasmic receptor domain, which in turn results in the recruitment of STAT proteins to the phosphorylated receptor. The recruited STATs are then also phosphorylated by the activated, receptor-associated JAK proteins, and each of them then homo- or hetero-dimerizes with another similarly phosphorylated STAT protein. Upon dimerization, the STAT proteins translocate to the cell nucleus and bind to specific DNA recognition sequences in the genome, thereby activating gene expression. See, e.g., Rane & Reddy, Oncogene 19:5662-5679 (2000), and references cited therein.

The cytoplasmic domains of transmembrane receptors associate with JAKs via JAK binding sites located close to the cell membrane. JAK-mediated phosphorylation of the intracellular receptor domain creates binding sites for the Src homology 2 (SH2) domains of STAT proteins. Binding of STAT proteins is followed by mostly tyrosine phosphorylation on key STAT protein residues, which then leads to the translocation of the phosphorylated STAT proteins to the cell nucleus.

Many transmembrane receptors and corresponding ligands have been reported to be involved in JAK-STAT signaling. See, e.g., Murray, Journal of Immunology 178: 2623-2629 (2007); Kubler, Australian Prescriber 37:154-157 (2014); see also O'Shea et al., Annals of the Rheumatic Diseases 72:ii111-ii115. For example, interleukin-15 has been reported to signal through the JAK-STA pathway via activating JAK3. See Krolopp et al., Frontiers in Physiology 7:626 (2016).

Janus kinases (JAKs) are non-receptor tyrosine kinases that play a critical role in cytokine signaling in mammals. The mammalian JAK family of kinases consists of Janus kinase 1 (JAK1), Janus kinase 2 (JAK2), Janus kinase 3 (JAK3) and tyrosine kinase 2 (TYK2). See U.S. Pat. No. 7,122,552, which is hereby incorporated by reference in its entirety. It is thought that JAK proteins do not operate alone, but that each transmembrane receptor requires at least two associated JAK proteins in order to signal. JAK proteins may operate in combinations of two JAK proteins of the same type (e.g., JAK2/JAK2) or of different types (e.g., JAK1/JAK3). JAK3 is thought to primarily signal in combination with JAK1. See Kubler, Australian Prescriber 37:154-157 (2014); see also Murray, Journal of Immunology 178:2623-2629 (2007).

All JAK proteins are characterized by seven so-called Janus homology domains (JH1-7). JH1 is the JAK proteins' tyrosine kinase domain and includes conserved residues the phosphorylation of which is important for the activation of the proteins' kinase activity. The JH2 domain is structurally similar to a kinase domain. JH2 does not have kinase activity by itself, however, but contributes to the activity of the JH1 domain. The JH3 and JH4 domains are homologous to Src-homology-2 (SH2) domains. The JH4 domain in conjunction with the JH5-7 domains facilitates the JAK proteins' binding to activated transmembrane receptors.

JAK1 and JAK2 are involved in a broad range of functions including host defense, haematopoiesis, neural development and growth. By contrast, JAK3 and TYK2 have a narrower role in the immune response. JAK3 is predominantly expressed in haematopoietic cells and is critical for signal transduction of interleukins integral to lymphocyte activation, function and proliferation. See Kubler, Australian Prescriber 2014:154-157 (2014).

Many genes have been reported to be regulated via the JAK-STAT pathway, including, for example, GATA3 CD23, Thy, Gp49 and Nfil3. See Murray, Journal of Immunology 178:2623-2629 (2007).

JAK Inhibitors

A number of JAK inhibitors have been reported. For example, the JAK1 inhibitor oclacitinib has been approved for the control of pruritus associated with allergic dermatitis and control of atopic dermatitis in dogs at least 12 months of age. See Gonzales et al., Journal of Veterinary Pharmacology and Therapeutics 37: 317-324 (2014); see also Prescribing Information for the Apoquel® Oclacitinib Maleate Drug Product (revised 2013). The JAK1/JAK2 inhibitor ruxolitinib (INCB018424) has been approved for the treatment of (1) intermediate or high-risk myelofibrosis, including primary myelofibrosis, post-polycythemia vera myelofibrosis and post-essential thrombocythemia myelofibrosis, and (2) polycythemia vera who have had an inadequate response to or are intolerant of hydroxyurea. See Prescribing Information for the Jakafi® Ruxolitinib Phosphate Drug Product (revised 2016). And the inhibitor tofacitinib (CP-690550) has been approved for the treatment of adult patients with moderately to severely active rheumatoid arthritis who have had an inadequate response or intolerance to methotrexate. Tofacitinib is currently marketed in its citrate salt form by Pfizer under the tradename Xeljanz®. See Prescribing Information for the Xeljanz Tofacitinib Citrate Drug Product (revised 2016).

A number of other JAK inhibitors are currently being evaluated in pre-clinical studies or clinical trials, including the following compounds: momelotinib (GS-0387, CYT-387), Baricitinib (LY-3009104, previously INCB028050), Filgotinib (GLPG-0634), Gandotinib (LY-2784544), Lestaurtinib (CEP-701), Momelotinib (GS-0387, CYT-387), Pacritinib (SB1518), PF-04965842, Upadacitinib (ABT-494), Peficitinib (ASP015K, JNJ-54781532), Cucurbitacin I (JSI-124), CHZ868, Fedratinib (TG101348; SAR302503), AZD1480; Decernotinib (VX-509; VRT-831509), Solcitinib (GSK-2586184; GLPG-0778), AC430, BMS-911543 and AG490. See, e.g., Furumoto & Gadina, BioDrugs 27:431-438 (2013).

Without wishing to be bound by any particular theory, tofacitinib has been reported to potently inhibit signaling through JAK1 and JAK3 with 5-100 fold selectivity over JAK2 in cellular assays. Tofacitinib has also been reported to inhibit recombinant human JAK1, 2, 3 and TYK2 in vitro with $IC_{50}$ (nM) values of 3.2±1.4, 4.1±0.4, 1.6±0.2 and 340±6.0, respectively. These results were interpreted to mean that for each JAK family member, tofacitinib competes with ATP for binding to the active site of the kinase domain. Tofacitinib has also been reported to inhibit cytokine signaling in human whole blood with the following specificities: IL-2 (mediated by JAK 1/3 heterodimer, readout pSTAT5)–$IC_{50}$ (nM) 28±5, IL-4 (mediated by JAK 1/3 heterodimer, readout pSTAT6)–$IC_{50}$ (nM) 50±5, IL-7 (mediated by JAK 1/3 heterodimer, readout pSTAT5)–$IC_{50}$ (nM) 38±9, IL-6 (mediated by JAK 1/2 heterodimer, readout pSTAT1)–$IC_{50}$ (nM) 54±7, and IL-6 (mediated by JAK 1/2 heterodimer, readout pSTAT3)–$IC_{50}$ (nM) 367±49. See Meyer et al., Journal of Inflammation 7:41 (2010).

Tofacitinib has been shown to inhibit the in vitro activities of JAK1/JAK2, JAK1/JAK3, and JAK2/JAK2 combinations with $IC_{50}$ of 406, 56, and 1377 nM, respectively. The relevance of specific JAK combinations to therapeutic effectiveness is not known. See Prescribing Information for the Xeljanz® Tofacitinib Citrate Drug Product (revised 2016).

Tofacitinib citrate has been approved for the treatment of adult patients with moderately to severely active rheumatoid arthritis (RA) who have had an inadequate response or intolerance to methotrexate. Tofacitinib citrate has been approved for use as a monotherapy or in combination with methotrexate or other nonbiologic disease-modifying antirheumatic drugs (DMARDs).

Tofacitinib citrate is a white to off-white powder with the following chemical name: (3R,4R)-4-methyl-3-(methyl-7H-pyrrolo[2,3-d]pyrimidin-4-ylamino)-β-oxo-1-piperidinepropanenitrile, 2-hydroxy-1,2,3-propanetricarboxylate (1:1). The solubility of tofacitinib citrate in water is 2.9 mg/mL.

Tofacitinib citrate has a molecular weight of 504.5 Daltons (or 312.4 Daltons as the tofacitinib free base) and a molecular formula of $C_{16}H_{20}N_6O \cdot C_6H_8O_7$. The chemical structure of tofacitinib citrate is as follows:

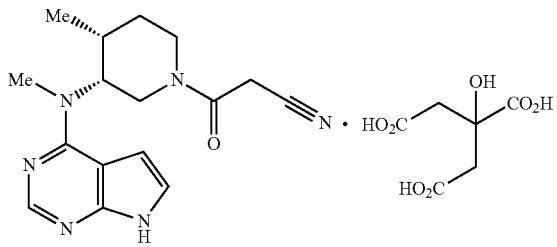 [SMILES: C[C@@H]1CCN(C(=O)CC#N)C[C@@H]1N(C)c1ncnc2[nH]ccc12 ; O=C(O)CC(O)(CC(=O)O)C(=O)O]

Tofacitinib citrate as approved for the treatment of RA is supplied for oral administration as white round, immediate-release film-coated tablets including 8 mg tofacitinib citrate (equivalent to 5 mg tofacitinib free base). Each tablet of tofacitinib citrate contains additionally the following excipients: microcrystalline cellulose, lactose monohydrate, croscarmellose sodium, magnesium stearate, HPMC 2910/Hypromellose 6 cP, titanium dioxide, macrogol/PEG3350, and triacetin.

Tofacitinib citrate as approved for the treatment of RA is also supplied for oral administration as pink, oval, extended release film-coated tablets with a drilled hole at one end of the tablet band including 17.77 mg tofacitinib citrate (equivalent to 11 mg tofacitinib free base). Each tablet of tofacitinib citrate contains additionally the following excipients: sorbitol, hydroxyethyl cellulose, copovidone, magnesium stearate, cellulose acetate, hydroxypropyl cellulose, HPMC 2910/Hypromellose, titanium dioxide, triacetin, and red iron oxide.

The printing ink on these extended release film-coated tablets contains shellac glaze, ammonium hydroxide, propylene glycol, and ferrosoferric oxide/black iron oxide. See Prescribing Information for the Xeljanz® Tofacitinib Citrate Drug Product (revised 2016).

The recommended dose of tofacitinib citrate for the treatment of RA is 5 mg (calculated based on the weight of tofacitinib free base) (immediate-release tablet) twice daily or 11 mg (calculated based on the weight of tofacitinib free base) once daily (extended release tablet).

Tofacitinib citrate is commercially available from Pfizer in the form of the Xeljanz® drug product. The synthesis of tofacitinib free base, tofacitinib citrate, and other salts of tofacitinib, as well as the manufacture of the pharmaceutical compositions and dosage forms disclosed herein are known to those skilled in the art, and described for example in U.S. Pat. Nos. 6,956,041; 7,091,208; and 7,265,221; which are hereby incorporated by reference in their entireties.

Tofacitinib has been reported to primarily inhibit JAK1 and JAK3. In some embodiments of the present invention, the JAK inhibitor is a JAK3 inhibitor. Non-limiting examples of JAK3 inhibitors and their bioactivity and synthesis are disclosed in U.S. Pat. No. 6,495,556 and U.S. Published Patent Application No. 2004/0198750, which are hereby incorporated by reference in their entireties. The chemical structure of an exemplary JAK3 inhibitor is provided below:

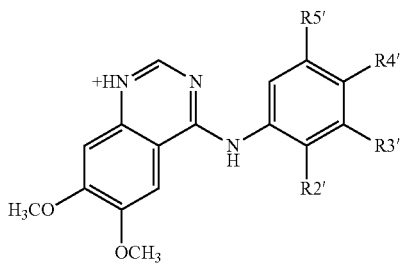

Each of moieties R2', R3', R4' and R5' may be H, OH, Br, or $CH_3$. In a preferred embodiment, moieties R2', R3', R4' and R5' are H, H, OH and H, respectively. See U.S. Pat. No. 6,495,556 (compound WHI-P131). In a preferred embodiment, moieties R2', R3', R4' and R5' are H, Br, OH and H, respectively. See U.S. Pat. No. 6,495,556 (compound WHI-P154).

Pharmaceutical Compositions

The present invention also provides pharmaceutical compositions including a JAK inhibitor, which in a non-limiting example is tofacitinib citrate, and a pharmaceutically acceptable excipient.

Examples of excipients that can be used in the pharmaceutical compositions provided herein are disclosed for example in U.S. Publication No. 2014/0271842 and in Handbook of Pharmaceutical Excipients, 3$^{rd}$ Edition, Edited by A.H. Kibbe, American Pharmaceutical Association and Pharmaceutical press (2000), which are hereby incorporated by reference in their entireties.

Other examples of excipients that can be used in the pharmaceutical compositions provided herein include, but are not limited to, binders, diluents, disintegrants, and lubricants. Binders suitable for use in pharmaceutical compositions include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of diluents suitable for use in the pharmaceutical compositions provided herein include, but are not limited to, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or diluent in pharmaceutical compositions provided herein is typically present in from about 50 to about 99 weight percent of the pharmaceutical composition or dosage form.

Examples of disintegrants that can be used in pharmaceutical compositions provided herein include, but are not limited to, alginic acid, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Examples of lubricants that can be used in pharmaceutical compositions provided herein include, but are not limited to, talc, calcium stearate, magnesium stearate, mineral oil, light mineral oil, polyethylene glycol, other glycols, stearic acid, sodium lauryl sulfate, hydrogenated vegetable oil (e.g., peanut oil, cottonseed oil, sunflower oil, sesame oil, olive oil, corn oil, and soybean oil), zinc stearate, and mixtures thereof.

Glycerin may be used as a humectant or for additional purposes. Ethyl oleate may be used as a solvent or for additional purposes. Ethyl laureate and agar may also be used as excipients.

Additional excipients that may be used in the pharmaceutical compositions provided herein include lactose monohydrate; HPMC 2910/Hypromellose 6 cP; titanium dioxide; macrogel/PEG3350; triacetin; hydroxyethyl cellulose; copovidone; hydroxypropyl cellulose; HPMC 2910/Hypromellose.

In some embodiments of the present invention, a binder, diluents, disintegrant or lubricant is present in the pharmaceutical compositions provided herein from about 3 to about 95, from about 3 to about 15, from about 15 to about 25, from about 25 to about 45, from about 45 to about 60, from about 60 to about 80, or from about 80 to about 95 weight percent of the pharmaceutical composition or dosage form.

In some embodiments of the present invention, the pharmaceutical composition includes one JAK inhibitor. In some embodiments of the present invention, the pharmaceutical composition includes a plurality of different JAK inhibitors. In some embodiments of the present invention, the pharmaceutical composition includes a therapeutic agent that is not a JAK inhibitor.

In some embodiments of the present invention, the JAK inhibitor is tofacitinib or a pharmaceutically acceptable salt thereof. In a preferred embodiment of the present invention, the JAK inhibitor is tofacitinib citrate.

In some embodiments of the present invention, tofacitinib citrate is present in the pharmaceutical compositions from about 1 to about 10, from about 10 to about 20, from about 20 to about 40, from about 40 to about 60, or from about 60 to about 90 weight percent of the pharmaceutical compositions.

The pharmaceutical compositions of the present invention can be prepared by any of the methods of pharmacy generally known in the art. In general, pharmaceutical compositions and dosage forms are prepared by uniformly and intimately admixing the active pharmaceutical ingredients with liquid carriers, finely divided solid carriers, or both, and then shaping the product into the desired presentation if necessary.

A pharmaceutical composition in accordance with the invention may be prepared, packaged, and/or sold in bulk, as a single dosage unit, and/or as a plurality of single dosage units.

Dosage Forms

According to the present invention, the pharmaceutical compositions disclosed herein may be provided in any of the dosage forms commonly known in the art. The dosage forms contemplated by the present invention can therefore take the form of tablets, capsules, pills, solutions, suspensions, emulsion, powders and the like. Such dosage forms can be prepared by any of the methods of pharmacy generally known in the art. See for example Remington: The Science and Practice of Pharmacy, 21st Edition (Lippincott, Williams & Wilkins, Baltimore, Md., 2006). Because of the ease of administration, tablets and capsules for oral administration are preferred. If desired, tablets can be coated by standard aqueous or nonaqueous techniques.

In general, dosage forms are prepared by uniformly and intimately admixing the active pharmaceutical ingredients with liquid carriers, finely divided solid carriers, or both, and then shaping the resulting pharmaceutical composition into the desired presentation if necessary. For example, a tablet can be prepared by compression or molding.

In some embodiments of the present invention, the dosage units are provided in an immediate release dosage form. In other embodiments of the present invention, the dosage units are provided in an extended and/or controlled release dosage form.

An immediate release dosage unit is a dosage unit containing an active pharmaceutical ingredient the release of which is not extended or controlled. Typically, these dosage units release their active pharmaceutical ingredient relatively quickly once the dosage unit has been administered. By contrast, extended and controlled release dosage units release their active pharmaceutical ingredient over an extended period of time and at certain physiological conditions, respectively. Controlled release of an active pharmaceutical ingredient can be stimulated by various conditions including, but not limited to, pH, temperature, enzymes, water, or other physiological conditions or agents.

The manufacture of immediate release dosage forms and extended and/or controlled release dosage forms is widely known in the art, and a person having ordinary skill in the art would know how to apply this general knowledge to the manufacture of such dosage forms including JAK inhibitors, for example tofacitinib citrate. Exemplary extended and/or controlled release dosage forms are disclosed for example in U.S. Pat. Nos. 9,669,022 and 9,629,837, which are hereby incorporated by reference in their entirety.

Various approaches are known in the art to prepare extended release dosage forms. For example, extended release may be achieved by embedding the active pharmaceutical ingredient in an extended release polymer. Non-limiting examples of such polymers are disclosed in U.S. Pat. No. 9,629,837, which is hereby incorporated by reference in its entirety.

Various approaches are also known in the art to prepare controlled release dosage forms. For example, controlled release may be achieved by providing dosage forms such as pellets, tablets and capsules with a controlled release coating that breaks down under certain conditions over time and then, once disintegrated, allows for the release of the underlying active pharmaceutical ingredient from the dosage unit. Controlled release may also be achieved based on the use of a controlled release matrix in which the active pharmaceutical ingredient is embedded.

Non-limiting examples of suitable materials for controlled (for example based on pH) release coatings according to the invention include shellac, cellulose acetate phthalate (CAP), polyvinyl acetate phthalate (PVAP), hydroxypropyl methylcellulose phthalate, and methacrylic acid ester copolymers, zein, and the like. See U.S. Pat. No. 9,669,022, which is hereby incorporated by reference in its entirety.

Non-limiting examples of suitable controlled-release materials which may be included in a controlled-release matrix according to the invention include: hydrophilic and/or hydrophobic materials, such as gums, cellulose ethers, acrylic resins, protein derived materials, waxes, shellac, and oils such as hydrogenated castor oil, hydrogenated vegetable oil. However, any pharmaceutically acceptable hydrophobic or hydrophilic controlled-release material which is capable of imparting controlled-release of the JAK inhibitors may be used in accordance with the present invention. Exemplary controlled-release polymers include alkylcelluloses such as ethylcellulose, acrylic and methacrylic acid polymers and copolymers, and cellulose ethers, especially hydroxyalkylcelluloses (especially hydroxypropylmethylcellulose) and carboxyalkylcelluloses. Examplary acrylic and methacrylic acid polymers and copolymers include methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers.

Specific examples of techniques and pharmaceutically acceptable excipients that may be used to formulate oral extended and/or controlled release dosage forms are also described in the Handbook of Sustained Release Dosage Form, LAP Lambert Acad. Publ., 2011, and the Handbook of Pharmaceutical Controlled Release Technology, Marcel Dekker Inc, 2000, which are hereby incorporated by reference in their entireties.

Many controlled release dosage units are designed to initially release an amount of active pharmaceutical ingredient that promptly produces the desired therapeutic effect, and to gradually and continually release the remaining amount of active pharmaceutical ingredient to maintain this level of therapeutic effect over an extended period of time. Thus, strictly speaking, this type of dosage unit is a combination of an immediate release unit and an extended release unit. These and other types of combinations of an immediate release unit and an extended release unit are also within the scope of the present invention.

In some embodiments of the present invention, the dosage unit is an immediate-release tablet including the following excipients: microcrystalline cellulose, lactose monohydrate, croscarmellose sodium, magnesium stearate, HPMC 2910/Hypromellose 6 cP, titanium dioxide, macrogol/PEG3350, and triacetin.

In some embodiments of the present invention, the dosage unit is an extended release tablet including the following excipients: sorbitol, hydroxyethyl cellulose, copovidone, magnesium stearate, cellulose acetate, hydroxypropyl cellulose, HPMC 2910/Hypromellose, titanium dioxide, triacetin, and red iron oxide. Printing ink contains shellac glaze, ammonium hydroxide, propylene glycol, and ferrosoferric oxide/black iron oxide.

In some embodiments of the present invention, microcrystalline cellulose is present in the dosage unit (e.g., tablet) provided herein in an amount of from about 100 to about 400 mg. In a preferred embodiment, microcrystalline cellulose is present in the dosage unit (e.g., tablet) provided herein in an amount of about 123 or about 315 mg.

In some embodiments of the present invention, lactose monohydrate is present in the dosage unit (e.g., tablet) provided herein in an amount of from about 50 to about 170 mg. In a preferred embodiment, lactose monohydrate is present in the dosage unit (e.g., tablet) provided herein in an amount of about 61 or about 157 mg.

In some embodiments of the present invention, croscarmellose sodium is present in the dosage unit (e.g., tablet) provided herein in an amount of from about 5 to about 17 mg. In a preferred embodiment, croscarmellose sodium is present in the dosage unit (e.g., tablet) provided herein in an amount of about 6 or about 15 mg.

In some embodiments of the present invention, magnesium stearate is present in the dosage unit (e.g., tablet) provided herein in an amount of from about 1.8 to about 5.5 mg. In a preferred embodiment, magnesium stearate is present in the dosage unit (e.g., tablet) provided herein in an amount of about 2 or about 5 mg.

In some embodiments of the present invention, sorbitol is present in the dosage unit (e.g., tablet) provided herein in an amount of from about 140 to about 160 mg. In a preferred embodiment, sorbitol is present in the dosage unit (e.g., tablet) provided herein in an amount of about 152 mg.

In some embodiments of the present invention, hydroxyethyl cellulose is present in the dosage unit (e.g., tablet) provided herein in an amount of from about 14 to about 18 mg. In a preferred embodiment, hydroxyethyl cellulose is present in the dosage unit (e.g., tablet) provided herein in an amount of about 16 mg.

In some embodiments of the present invention, copovidone is present in the dosage unit (e.g., tablet) provided herein in an amount of from about 11 to about 13 mg. In a preferred embodiment, copovidone is present in the dosage unit (e.g., tablet) provided herein in an amount of about 12 mg.

In some embodiments of the present invention, magnesium stearate is present in the dosage unit (e.g., tablet) provided herein in an amount of from about 1.8 to about 2.2 mg. In a preferred embodiment, magnesium stearate is present in the dosage unit (e.g., tablet) provided herein in an amount of about 2 mg.

In some embodiments of the present invention, cellulose acetate is present in the dosage unit (e.g., tablet) provided herein in an amount of from about 8.2 to about 8.6 mg. In a preferred embodiment, cellulose acetate is present in the dosage unit (e.g., tablet) provided herein in an amount of about 8.4 mg.

In some embodiments of the present invention, hydroxypropyl cellulose is present in the dosage unit (e.g., tablet) provided herein in an amount of from about 5.4 to about 5.8 mg. In a preferred embodiment, hydroxypropyl cellulose is present in the dosage unit (e.g., tablet) provided herein in an amount of about 5.6 mg.

In some embodiments of the present invention, the dosage unit includes one JAK inhibitor. In some embodiments of the present invention, the dosage unit includes a plurality of JAK inhibitors. In some embodiments of the present invention, the dosage unit includes a therapeutic agent that is not a JAK inhibitor.

In some embodiments of the present invention, the JAK inhibitor is tofacitinib or a pharmaceutically acceptable salt thereof. In a preferred embodiment of the present invention, the JAK inhibitor is tofacitinib citrate.

In some embodiments of the present invention, tofacitinib citrate is present in the dosage units provided herein in an amount from about 1 to about 2 mg per dosage unit, from about 2 to about 5 mg per dosage unit, from about 5 to about 10 mg per dosage unit, from about 10 to 15 mg per dosage unit, from about 15 to 25 mg per dosage unit, or from about 25 to 50 mg per dosage unit, (weights are calculated based on the weight of tofacitinib free base).

In a preferred embodiment of the present invention, tofacitinib citrate is present in the dosage units provided herein in an amount of about 8 mg (equivalent to about 5 mg tofacitinib free base) per dosage unit, wherein the dosage unit is an immediate-release film-coated tablet containing the following excipients: microcrystalline cellulose, lactose monohydrate, croscarmellose sodium, magnesium stearate, HPMC 2910/Hypromellose 6 cP, titanium dioxide, macrogol/PEG3350, and triacetin. In an even more preferred embodiment of the present invention, tofacitinib citrate is present in the dosage units provided herein in an amount of 8 mg (equivalent to 5 mg tofacitinib free base).

In a preferred embodiment of the present invention, tofacitinib citrate is present in the dosage units provided herein in an amount of about 17.77 mg (equivalent to about 11 mg tofacitinib free base) per dosage unit, wherein the dosage unit is an extended release film-coated tablet containing the following excipients: sorbitol, hydroxyethyl cellulose, copovidone, magnesium stearate, cellulose acetate, hydroxypropyl cellulose, HPMC 2910/Hypromellose, titanium dioxide, triacetin, and red iron oxide. In an even more preferred embodiment of the present invention, tofacitinib citrate is present in the dosage units provided herein in an amount of 17.77 mg (equivalent to 11 mg tofacitinib free base).

Concentrations of active pharmaceutical ingredients (e.g., tofacitinib) and excipients may be measured in accordance with methods and techniques that are standard in the pharmaceutical art and therefore not further detailed herein.

Relative amounts of active pharmaceutical ingredient, excipient, and/or any additional ingredients in a pharmaceutical composition and dosage unit in accordance with the invention may vary, depending upon the identity, size, and/or condition of the subject treated and/or depending upon the route by which the composition is to be administered. By way of example, the composition may comprise between 0.1% and 100% (w/w) active pharmaceutical ingredient.

Also within the scope of the present invention are pharmaceutical compositions and dosage forms that include a Janus kinase inhibitor and one or more additional therapeutic agents, which may or may not be a different Janus kinase inhibitor. In some embodiments of the present invention, the additional therapeutic agent is a an agent commonly used for treatment of IDDM.

Routes of Administration and Dosing Regimen

JAK inhibitors, or a pharmaceutically acceptable salts or esters thereof, can be administered by any convenient route commonly known in the art. Methods of administration include, but are not limited to, oral, parenteral, intradermal, intramuscular, intraperitoneal, intravenous, subcutaneous, intranasal, epidural, sublingual, intracerebral, intravaginal, transdermal, transmucosal, rectal, or topical administration, or administration by inhalation. The mode of administration is left to the discretion of the practitioner. In most instances, administration will result in the release of a compound into the bloodstream.

In a preferred embodiment of the present invention, the JAK inhibitor is administered orally.

Suitable dosages of JAK inhibitors (or pharmaceutically acceptable salts or esters thereof) for administration within the scope of the present invention include, but are not limited to, JAK inhibitor dosages (or dosages of pharmaceutically acceptable salts or esters thereof) of between about 1 mg and about 10 mg administered to the subject once or twice daily. In some embodiments of the present invention, suitable dosages include JAK inhibitor dosages (or dosages of pharmaceutically acceptable salts or esters thereof) of between about 5 mg and about 8 mg administered to the subject once or twice daily.

In some embodiments of the present invention, suitable dosages include JAK inhibitor dosages (or dosages of pharmaceutically acceptable salts or esters thereof) of between about 10 mg and about 17 mg administered to the subject once or twice daily. In some embodiments of the present invention, suitable dosages include JAK inhibitor dosages (or dosages of pharmaceutically acceptable salts or esters thereof) of between about 17 mg and about 25 mg administered to the subject once or twice daily. In some embodiments of the present invention, suitable dosages include JAK inhibitor dosages (or dosages of pharmaceutically acceptable salts or esters thereof) of between about 25 mg and about 50 mg administered to the subject once or twice daily.

Also contemplated within the scope of the present invention are other dosing regimen, non-limiting examples of which are thrice-daily and four-times daily administration of a JAK inhibitor, weekly, biweekly and thrice-weekly administration of a JAK inhibitor, and monthly, bimonthly and thrice-monthly administration of a JAK inhibitor.

In a preferred embodiment of the present invention, an immediate-release tablet containing tofacitinib citrate in an amount of 5 mg (calculated based on the weight of tofacitinib free base) is administered twice daily, or an extended-release tablet containing tofacitinib citrate in an amount of 11 mg (calculated based on the weight of tofacitinib free base) is administered once daily.

In a preferred embodiment of the present invention, two immediate-release tablets each containing tofacitinib citrate in an amount of 5 mg (calculated based on the weight of tofacitinib free base) are administered twice daily.

In some embodiments of the present invention, the commercially available tofacitinib in accordance with the present invention is administered in accordance with the dosage forms approved by the Food and Drug Administration (FDA) for this type of product.

Intravenous Immunoglobulin (IVIG)

Intravenous immunoglobulin (WIG) is a mixture of antibodies (immunoglobulins) combined from a variety of donors, and is used as a replacement therapy in immune-deficient individuals. Less intuitively, IVIG can also be used to suppress the pathological immune responses that occur in patients with autoimmunity. See Schwab & Nimmerjahn, Nature Reviews Immunology 13:176-189 (2013); see also Heiner, Review of Infectious Diseases 8:S391-395.

Intravenous immunoglobulin is commercially available from numerous sources generally known in the art. For example Grifols Therapeutics Inc., NC, USA, markets the GAMUNEX®-C liquid 10% immune globulin product for injection in humans that has been approved by the FDA for primary humoral immunodeficiency (PI) in patients 2 years of age and older, idiopathic thrombocytopenic purpura (ITP), and chronic inflammatory demyelinating polyneuropathy (CIDP).

The GAMUNEX®-C product is a sterile solution for injection supplied in 1 g protein (10 mL), 2.5 protein g (25 mL), 5 g protein (50 mL), 10 g protein (100 mL), 20 g protein (200 mL), or 40 g protein (400 mL) single use bottles. GAMUINEX-C® consists of 9%-11% protein in 0.16-0.24 M glycine.

The GAMUNEX®-C product contains trace levels of fragments, IgA (average 0.046 mg/mL), and IgM. The distribution of IgG subclasses is similar to that found in normal serum. The main component of the GAMUNEX®-C product is IgG (≥98%) with a sub-class distribution of IgG1, IgG2, IgG3 and IgG4 of approximately 62.8%, 29.7%, 4.8% and 2.7%, respectively.

The GAMUNEX®-C product is made from large pools of human plasma by a combination of cold ethanol fractionation, caprylate precipitation and filtration, and anion-exchange chromatography. Isotonicity is achieved by the addition of glycine. The GAMUNEX®-C product is incubated in the final container (at the low pH of 4.0-4.3). The product is intended for intravenous administration and may be administered subcutaneously in the treatment of PI.

The GAMUNEX®-C product is indicated for intravenous or subcutaneous administration. For intravenous administration, the dose of GAMUNEX®-C for patients with PI is 300 mg/kg to 600 mg/kg body weight (3 mL/kg to 6 mL/kg) administered every 3 to 4 weeks. The dosage may be adjusted over time to achieve the desired trough levels and clinical responses. The recommended initial infusion rate is 1 mg/kg/min (0.01 mL/kg/min). If the infusion is well-tolerated, the rate may be gradually increased to a maximum of 8 mg/kg/min (0.08 mL/kg/min). For subcutaneous administration to patients with PI, the dose of the GAMUNEX®-C product is determined and possibly adjusted over time based on prior administration of other IVIG and the patient's clinical response, in accordance with protocols/methods commonly known in the art.

The rate of administration of the GAMUNEX®-C product for intravenous administration to patients with PI is 1 mg/kg/min for the first 30 minutes, which is then increased up to a maximum of 8 mg/kg/min if tolerated.

See Prescribing Information for the GAMUNEX®-C Drug Product (revised 2016).

Pharmaceutical Compositions, Dosage Forms, Routes of Administration and Dosing Regimen In a preferred embodiment, the intravenous immunoglobulin is administered to a subject in the form of a sterile solution for injection supplied in 1 g immunoglobulin (10 mL), 2.5 g immunoglobulin (25 mL), 5 g immunoglobulin (50 mL), 10 g immunoglobulin (100 mL), 20 g immunoglobulin (200 mL), or 40 g immunoglobulin (400 mL) single use bottles, wherein the immunoglobulin is present at a concentration of 9%-11% w/v in 0.16-0.24 M glycine.

The pharmaceutical compositions, dosage forms and routes of administration of intravenous immunoglobulin contemplated as part of the present invention are not limited to pharmaceutical compositions that are particular liquid injectables for intravenous or subcutaneous administration, but include all types of pharmaceutical compositions, dosage forms and routes of administration commonly known and used in the art for immunoglubulins, as further described in connection with the disclosure of pharmaceutical compositions, dosage forms and routes of administration of therapeutic agents that destroy B lymphocytes, which is also applicable to intravenous immunoglobulin.

In some embodiments of the present invention, intravenous immunoglobulin (IVIG) is administered by injection.

In some embodiments of the present invention, intravenous immunoglobulin (IVIG) is administered by infusion.

In some embodiments of the present invention, the dose of intravenous immunoglobulin for patients with IDDM is about 0.01, about 0.1, about 1, about 2, about, 3, about, 4, about 5, about 10, about 50 or about 100 mg/kg body weight of the patient.

In some embodiments of the present invention, a dose of intravenous immunoglobulin is administered once daily; or once every 2, 3, 4, 5, 6 or 7 days; or once every week; or once every 2, 3, 4, 5, 6, 7, 8, 9 or 10 weeks, for a total 1, 2, 3, 4, 5, 6, 7, 8, 9, or 10 doses.

In some embodiments of the present invention, a dose of intravenous immunoglobulin is administered at the beginning of the dosing regimen on several consecutive days (e.g., 2, 3, 4, 5, 6, 7, 8, 9 or 10 days), and then administered every 1, 2, 3, 4, 5, 6, 7, 8, 9, or 10 weeks. In a preferred embodiment of the present invention, a dose of intravenous immunoglobulin is administered on each of days 1, 2 and 3 at the beginning of the dosing regimen. In a preferred embodiment of the present invention, doses of intravenous immunoglobulin are administered every 3 weeks after the administration of doses of intravenous immunoglobulin on 3 consecutive days at the beginning of the dosing regimen. In a preferred embodiment of the present invention, these first three doses are 1 or 2 mg intravenous immunoglobulin.

In some embodiments of the present invention, the intravenous immunoglobulin in accordance with the present invention is administered in accordance with the dosage forms and dosing regimens approved by the FDA for this type of product.

Also within the scope of the present invention are pharmaceutical compositions and dosage forms that include intravenous immunoglobulin and one or more additional therapeutic agents.

Therapeutic Agent that Destroys B Lymphocytes

The present invention provides a method of treating insulin-dependent diabetes mellitus in a subject including administering to the subject a therapeutically effective amount of a Janus kinase inhibitor, or a pharmaceutically acceptable salt or ester thereof, therapeutically effective amount of intravenous immunoglobulin, or therapeutically effective amount of a therapeutic agent that destroys B lymphocytes, or combinations thereof.

In some embodiments of the present invention, the therapeutic agent that destroys B lymphocytes is an anti-CD20 antibody agent. In a preferred embodiment, the anti-CD20 antibody agent is the antibody rituximab, or antibody fragments thereof.

B-lymphocyte antigen CD20 corresponds to a phosphoprotein located on the surface of B-cells that has been reported to facilitate optimal B-cell immune responses. CD20 is targeted by a number of therapeutic antibodies that have been approved by the FDA for the treatment of a variety of conditions.

Rituximab is currently being marketed by Biogen Inc. and Genentech USA, Inc. under the tradename Rituxan®. Rituximab is a monoclonal antibody that binds to the CD20 antigen located on the surface of pre-B and mature B-lymphocytes. Upon binding to CD20, rituximab mediates B-cell lysis, possibly via complement dependent cytotoxicity (CDC) or antibody dependent cell mediated cytotoxicity (ADCC), resulting in destruction of B lymphocytes. See Prescribing Information for the Rituxan® Rituximab Drug Product (2016).

Rituximab is a murine/human chimeric monoclonal IgG1 kappa antibody directed to the CD20 antigen. Rituximab has an approximate molecular weight of 145 kD and a binding affinity for the CD20 antigen of approximately 8.0 nM. See Prescribing Information for the Rituxan® Rituximab Drug Product (2016).

The isolation, screening, and characterization of rituximab is taught by U.S. Pat. Nos. 5,736,137; 5,776,456 and 5,843,439, which are hereby incorporated by reference in their entireties.

Rituximab is produced in Chinese hamster ovary cells and provided as a sterile, clear, colorless, preservative-free liquid concentrate for intravenous administration. Rituximab is supplied at a concentration of 10 mg/mL in either 100 mg/10 mL or 500 mg/50 mL single-use vials. The rituximab is formulated in polysorbate 80 (0.7 mg/mL), sodium chloride (9 mg/mL), sodium citrate dihydrate (7.35 mg/mL), and water for injection. The pH is 6.5. Before use, an appropriate amount of the aforesaid rituximab concentrate is diluted to a final concentration of 1 mg/mL to 4 mg/mL in an infusion bag containing either 0.9% Sodium Chloride, USP, or 5% Dextrose in Water, USP. See Prescribing Information for the Rituxan® Rituximab Drug Product (2016).

B cells are believed to play a role in the pathogenesis of rheumatoid arthritis (RA) and associated chronic synovitis. In this setting, B cells may be acting at multiple sites in the autoimmune/inflammatory process, including through production of rheumatoid factor (RF) and other autoantibodies, antigen presentation, T-cell activation, and/or proinflammatory cytokine production. See Prescribing Information for the Rituxan® Rituximab Drug Product (2016).

Rituximab has been approved for the treatment of Non-Hodgkin's Lymphoma (NHL). Rituximab has also been approved for the treatment of Chronic Lymphocytic Leukemia (CLL), Rheumatoid Arthritis (RA), and Granulomatosis with Polyangiitis (GPA) (Wegener's Granulomatosis) and Microscopic Polyangiitis (MPA).

For the treatment of Non-Hodgkin's Lymphoma (NHL), the recommended dose of rituximab is 375 $mg/m^2$ as an intravenous infusion.

For the treatment of Chronic Lymphocytic Leukemia (CLL), the recommended dose is 375 $mg/m^2$ the day prior to the initiation of FC chemotherapy, then 500 $mg/m^2$ on Day 1 of cycles 2-6 (every 28 days).

For the treatment of NHL as a component of the Zevalin® drug product, rituximab is infused at 250 $mg/m^2$ within 4 hours prior to the administration of Indium-111-(In-111-) Zevalin and within 4 hours prior to the administration of Yttrium-90-(Y-90-) Zevalin.

For the treatment of Rheumatoid Arthritis (RA), rituximab is administered as two-1000 mg intravenous infusions separated by 2 weeks. Glucocorticoids administered as methylprednisolone 100 mg intravenous or its equivalent 30 minutes prior to each infusion are recommended to reduce the incidence and severity of infusion reactions. Subsequent courses are administered every 24 weeks or based on clinical evaluation, but not sooner than every 16 weeks. Rituxan is administered in combination with methotrexate.

For the treatment of Granulomatosis with Polyangiitis (GPA) (Wegener's Granulomatosis) and Microscopic Polyangiitis (MPA), rituximab is administered as a 375 $mg/m^2$ intravenous infusion once weekly for 4 weeks. Glucocorticoids administered as methylprednisolone 1000 mg intravenously per day for 1 to 3 days followed by oral prednisone 1 mg/kg/day (not to exceed 80 mg/day and tapered per clinical need) are recommended to treat severe vasculitis symptoms. This regimen begins within 14 days prior to or with the initiation of rituximab treatment and may continue during and after the 4 week course of rituximab treatment. See Prescribing Information for the Rituxan® Rituximab Drug Product (2016).

Non-limiting examples of other anti-CD20 therapeutic antibody agents that have been approved by the FDA for the treatment of a variety of conditions, or are in preclinical or clinical trials, include the following:

Obinutuzumab, which is a humanized anti-CD20 monoclonal antibody of the IgG1 subclass currently being marketed by Genentech, Inc. under the tradename Gazyva®; ofatumumab which is a human anti-CD20 monoclonal antibody of the IgG1 subclass currently being marketed by Novartis Pharmaceuticals Corporation under the tradename Arzerra®; ibritumomab tiuxetan, which is a murine anti-CD20 monoclonal antibody of the IgG1 subclass conjugated with the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine currently being marketed by Spectrum Pharmaceuticals, Inc., under the tradename Zevalin®; ocrelizumab, which is a humanized anti-CD20 monoclonal antibody of the IgG1 subclass currently being marketed by Genentech, Inc., under the tradename Ocrevus; tositumomab, which is a murine anti-CD20 monoclonal antibody (see Srinivasan & Mukherji, AJNR. American Journal of Neuroradiology 32:637-638 (2011)); ocaratuzumab, which is a humanized anti-CD20 monoclonal antibody (see Cheney et al., Monoclonal Antibodies 6:748-754 (2014)); TRU-015, which is a fusion protein derived from an anti-CD20 antibody (see Rubbert-Roth, Current Opinion in Molecular Therapeutics 12:115-123 (2010)); and veltuzumab, which is a humanized anti-CD20 monoclonal antibody (see Cang et al., Journal of Hematology & Oncology 5:64 (2012)).

Antibody Agents, Antibody Fragments & Antibody Conjugates

In some embodiments of the present invention, the therapeutic agent that destroys B lymphocytes is an anti-CD20 antibody agent. In a preferred embodiment, the anti-CD20 antibody agent is the antibody rituximab.

The term "anti-CD20 antibody agent" refers to an antibody agent that specifically binds to the CD20 antigen. Consistent with the definition of the term "antibody agent" elsewhere herein, an anti-CD20 antibody agent includes, but is not limited to, the following formats, all of which bind to the CD20 antigen: murine antibodies, chimeric antibodies (e.g., human/mouse), primatized antibodies, humanized antibodies, human antibodies, bi-specific antibodies, conjugated antibodies, single chain antibodies, and antibody fragments.

All of the antibody agent formats disclosed herein are widely used in the art and known by the person having ordinary skill in the art. Technologies for generating such formats (e.g., monoclonal antibodies and/or polyclonal antibodies) are well known in the art. See, e.g., Antibodies: A Laboratory Manual, Second edition, Edited by Edward A. Greenfield, Cold Spring Harbor Laboratory Press (2014).

It will be appreciated that a wide range of animal species can be used for the production of antisera, including rabbit, mouse, rat, hamster, guinea pig or goat. The animal species may be chosen based on the ease of manipulation, costs or the desired amount of sera, as would be known to one of skill in the art. It will be appreciated that antibody agents can also be produced transgenically through the generation of a mammal or plant that is transgenic for the immunoglobulin heavy and light chain sequences of interest. In connection with the transgenic production in mammals, antibodies can be produced in, and recovered from, the milk of goats, cows, or other mammals. See, e.g., U.S. Pat. No. 5,827,690, which is incorporated herein by reference in its entirety.

Antibody agents provided herein may be produced, for example, by utilizing a host cell system engineered to express a nucleic acid encoding an inventive antibody agent. Alternatively or additionally, antibody agents provided herein may be partially or fully prepared by chemical synthesis (e.g., using an automated peptide synthesizer).

Technologies for making and using polyclonal and monoclonal antibodies are described, e.g., in Harlow et al., Using Antibodies: A Laboratory Manual: Portable Protocol I. Cold Spring Harbor Laboratory (Dec. 1, 1998). Technologies for making modified antibody agents, such as, antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition).

Exemplary sources for antibody agent preparations suitable for the invention include, but are not limited to, conditioned culture medium derived from culturing a recombinant cell line that expresses a protein of interest; extracts of, e.g., bacteria, fungal cells, insect cells, transgenic plants or plant cells, transgenic animals or animal cells expressing a protein of interest; serum or ascites fluid of animals; and hybridoma or myeloma supernatants. Suitable bacterial cells include, but are not limited to, *Escherichia coli* cells. Examples of suitable *E. coli* strains include: HBIOI, DH5a, GM2929, JM109, KW251, NM538, NM539, and any other *E. coli* strain that fails to cleave foreign DNA. Suitable fungal host cells that can be used include, but are not limited to, *Saccharomyces cerevisiae*, *Pichia pastoris* and *Aspergillus* cells. Suitable insect cells include, but are not limited to, S2 Schneider cells, D. Mel-2 cells, SF9, SF21, High-5™ Mimic™-SF9, MGI and KCl cells. Suitable exemplary recombinant eukaryotic cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (He La), canine kidney cells, buffalo rat liver cells, human lung cells, human liver cells, mouse mammary tumor cells, TRI cells, MRC 5 cells, FS4 cells, and human hepatoma line (Hep G2). In a preferred embodiment of the present invention, rituximab is produced in Chinese hamster ovary cells.

Antibody agents of interest can be expressed using any appropriate vector. A variety of vectors (e.g., viral vectors) is known in the art. Cells into which such vectors can been introduced (or progeny of such cells) can be cultured according to general knowledge in the art (e.g., by using continuous or fed-batch culture systems). In some embodiments of the present invention, cells may be genetically engineered; technologies for genetically engineering cells to express engineered polypeptides (e.g., antibody agent polypeptides, as described herein) are well known in the art. See e.g. Ausubel et al., eds. (1990), Current Protocols in Molecular Biology (Wiley, New York).

In some embodiments of the present invention, the antibody agents provided herein may be purified, if desired, using filtration, centrifugation and/or a variety of chromatographic technologies such as HPLC or affinity chromatography. In some embodiments of the present invention, fragments of provided antibody agents are obtained by methods which include digestion with enzymes, such as pepsin or papain, and/or by cleavage of disulfide bonds by chemical reduction.

Based on one or more known antibodies, a person having ordinary skill in the art would know how to prepare corresponding antibody agents of the aforesaid formats such that they have the same binding activities as the known antibodies. See, e.g., Benny K. C. Lo (ed.), Antibody Engineering—Methods and Protocols, Humana Press 2004, and references cited therein.

Single-chain Fvs (scFvs) are widely known and used in the art. A single-chain Fv is a fusion protein of the variable regions of the heavy (VH) and light chains (VL) of immunoglobulins, often connected by a short linker peptide. See, e.g., Benny K. C. Lo (ed.), Antibody Engineering—Methods and Protocols, Humana Press 2004, and references cited therein. In some embodiments of the present invention, a scFv polypeptide is conjugated to a therapeutic agent or detection agent.

Bispecific antibodies are widely known and used in the art. Bispecific antibodies are artificial proteins that include fragments from two different antibodies and consequently bind to two different types of antigens. In some embodiments of the present invention, bispecific antibodies include two different immunoglobulin heavy chains and two different immunoglobulin light chains.

In some embodiments of the present invention, the anti-CD20 antibody agent comprises all CDRs of rituximab. A person having ordinary skill in the art would know how to identify the CDRs of rituximab and use them for the many antibody formats disclosed herein based on the disclosures in this specification and common knowledge in the art.

In some embodiments of the present invention, an antibody agent as described herein is associated with a payload entity and thereby forms a conjugate. In some embodiments of the present invention, a payload entity is or comprises a therapeutic agent. In some embodiments of the present invention, a payload entity is or comprises a detection agent.

Therapeutic agents can be or comprise any class of chemical entity including, for example, but not limited to, proteins, carbohydrates, lipids, nucleic acids, small organic molecules, non-biological polymers, metals, ions, radioisotopes, etc. In some embodiments of the present invention, the conjugated therapeutic agent is a radioisotope, a drug conjugate, a nanoparticle, an immune-toxin, or any other therapeutic payload. In some embodiments of the present invention, therapeutic agents for use in accordance with the present invention have one or more pharmacological activities.

Several technologies are generally known in the art for the attachment or conjugation of an antibody agent to a therapeutic or detection agent. Some attachment technologies involve the use of a metal chelate complex employing, for example, an organic chelating agent such as diethylenetriaminepentaacetic acid anhydride (DTPA); ethylenetriaminetetraacetic acid; N-chloro-p-toluenesulfonamide; and/or tetrachloro-3a-6a-diphenylglycouril-3 attached to the antibody. See U.S. Pat. Nos. 4,472,509 and 4,938,948, each of which is incorporated herein by reference in its entirety. Provided antibody agents may also be reacted with an enzyme in the presence of a coupling agent such as glutaraldehyde or periodate.

It will be appreciated that the antibody agents provided herein may be engineered, produced, and/or purified in such a way as to improve characteristics and/or activities of the antibody agents. For example, improved characteristics of provided antibody agents include, but are not limited to, increased stability, improved binding affinity and/or avidity, increased binding specificity, increased production, decreased aggregation, decreased nonspecific binding, among others.

Pharmaceutical Compositions & Dosage Forms

The present invention also provides a pharmaceutical composition including a therapeutic agent that destroys B lymphocytes, an antibody agent, rituximab or an antibody fragment thereof, or other antibody agent formats as disclosed herein, and a pharmaceutically acceptable carrier.

The pharmaceutical compositions contemplated as part of the present invention are not limited to pharmaceutical compositions that can be administered to a subject by infusion or injection, but include all types of pharmaceutical compositions and dosage forms commonly known and used in the art.

Preferably, the therapeutic agent that destroys B lymphocytes (e.g., anti-CD20 antibody agent) provided herein is formulated as a sterile liquid pharmaceutical composition suitable for subcutaneous injection or intravenous infusion and/or injection. In some embodiments of the present invention, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments of the present invention, pharmaceutical compositions are diluted and/or reconstituted in water, sodium chloride solution, sodium acetate solution, benzyl alcohol solution, phosphate buffered saline, etc. In some embodiments of the present invention, powder should be mixed gently with the aqueous diluent (e.g., not shaken).

In some embodiments of the present invention, provided pharmaceutical compositions comprise one or more pharmaceutically acceptable excipients. In some embodiments of the present invention, pharmaceutical compositions comprise one or more preservatives. In some embodiments of the present invention, pharmaceutical compositions comprise no preservative. Excipients as used herein may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form and administration route desired. Remington's The Science and Practice of Pharmacy, 21st Edition, A. R. Gennaro, (Lippincott, Williams & Wilkins, Baltimore, Md., 2006) discloses a variety of excipients used in formulating pharmaceutical compositions and known techniques for the preparation thereof. Except insofar as any conventional excipient is incompatible with a substance or its derivatives in the pharmaceutical composition, such as by producing any undesirable biological effect or otherwise interacting in a deleterious manner with any other component(s) of the pharmaceutical composition, its use is contemplated to be within the scope of this invention.

In a preferred embodiment of the present invention, an antibody agent (e.g., rituximab) is provided as a sterile, clear, colorless, preservative-free liquid concentrate for intravenous administration. In this preferred embodiment, the antibody agent (e.g., rituximab) is supplied at a concentration of 10 mg/mL in either 100 mg/10 mL or 500 mg/50 mL single-use vials, which further contain polysorbate 80 (0.7 mg/mL), sodium chloride (9 mg/mL), sodium citrate dihydrate (7.35 mg/mL), and water for injection.

In some embodiments of the present invention, an antibody agent (e.g., rituximab) is provided at a concentration of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/mL In some embodiments of the present invention, an antibody agent (e.g., rituximab) is provided in a liquid concentrate for intravenous administration comprising 0.1, 02, 0.3, 0.4, 0.5, 0.7, 0.8, 0.9, 1.0, 1.1, 1.2, 1.3, 1.4, or 1.5 mg/mL polysorbate 80; 1, 2, 3, 4, 5, 6, 7, 8, 9, 10, 11, 12, 13, 14, or 15 mg/mL sodium chloride; 1, 2, 3, 4, 5, 6, 7, 7.35, 8, 9, 10, 11, 12, 13, or 14 mg/mL sodium citrate dihydrate; and water.

In a preferred embodiment of the present invention, an appropriate amount of the aforesaid concentrate of an antibody agent (e.g., rituximab) is diluted to a final concentration of 1 mg/mL to 4 mg/mL in an infusion bag containing either 0.9% Sodium Chloride, USP, or 5% Dextrose in Water, USP.

In some embodiments of the present invention, pharmaceutical compositions are provided in a form that can be refrigerated and/or frozen. In some embodiments of the present invention, pharmaceutical compositions are provided in a form that cannot be refrigerated and/or frozen. In some embodiments of the present invention, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments of the present invention, a solution should not be used if discolored or cloudy and/or if particulate matter remains after filtration.

Pharmaceutical compositions described herein may be prepared by any method known or hereafter developed in the art of pharmacology. In some embodiments of the present invention, such preparatory methods include the step of bringing an active pharmaceutical ingredient into association with one or more excipients and/or one or more other accessory ingredients, and then, if necessary and/or desirable, shaping and/or packaging the product into a desired single dosage unit or multiple dosage units.

A pharmaceutical composition in accordance with the invention may be prepared, packaged, and/or sold in bulk, as a single dosage unit, and/or as a plurality of single dosage units.

Relative amounts of active pharmaceutical ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active pharmaceutical ingredient.

Also within the scope of the present invention are pharmaceutical compositions and dosage forms that include two or more different therapeutic agents that destroy B lymphocytes, or one or more therapeutic agents that destroy B lymphocytes and one or more therapeutic agents that are not therapeutic agents that destroy B lymphocytes. In one embodiment of the present invention, the pharmaceutical compositions or dosage form includes one antibody agent wherein a subpopulation of this antibody agent is conjugated with a payload entity, and another subpopulation of this antibody agent is conjugated with a different type of payload entity.

Concentrations of active pharmaceutical ingredients (e.g., rituximab) and excipients may be measured in accordance with methods and techniques that are standard in the pharmaceutical art and therefore not further detailed herein. For example, the concentration of rituximab in a pharmaceutical composition or dosage form may be measured based on protein absorbance at 280 nm, or by using on enzyme-linked immunosorbent assay (ELISA). These and other approaches are widely known in the art and thus not further detailed herein.

Routes of Administration and Dosing Regimen

The pharmaceutical compositions and dosage forms of the therapeutic agents and antibody agents disclosed herein may be administered by any means commonly used in the art. In some embodiments of the present invention, antibody agent includes therapeutic agents that destroy B lymphocytes, for example rituximab or fragments thereof. In some embodiments of the present invention, the pharmaceutical composition and dosage form may be administered subcutaneously or intravenously.

Pharmaceutical compositions of the present invention may be administered by any appropriate route, as will be appreciated by those skilled in the art. In some embodiments of the present invention, a pharmaceutical composition including an antibody agent of the present invention is administered by an intravenous (IV), intramuscular (IM), intra-arterial, subcutaneous (SQ), transdermal, interdermal, intradermal, or intraperitoneal (IP) route. In some embodiments of the present invention, pharmaceutical compositions including antibody agents of the present invention may be administered via portal vein catheter.

In some embodiments of the present invention, the pharmaceutical composition including an antibody agent of the present invention (e.g., rituximab) is administered by injection. In some embodiments of the present invention, the pharmaceutical composition including an antibody agent of the present invention (e.g., rituximab) is administered by infusion.

In a preferred embodiment of the present invention, the pharmaceutical composition including an antibody agent of the present invention (e.g., rituximab) is administered intravenously.

In some embodiments of the present invention, pharmaceutical compositions including antibody agents (e.g., rituximab) in accordance with the invention may be administered at dosage levels sufficient to deliver from about 0.001 mg to about 100 mg, from about 0.01 mg to about 50 mg, from about 0.1 mg to about 40 mg, from about 0.5 mg to about 30 mg, or from about 1.0 mg to about 10 mg of antibody agent per kg subject body weight per day, per week, or per month to obtain the desired therapeutic effect.

In some embodiments of the present invention, pharmaceutical compositions including antibody agents (e.g., rituximab) in accordance with the invention may be administered at a dose of 1-50, 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, or 1450-1500 mg of antibody agent per $m^2$ subject surface area. In preferred embodiments, the dose is 250, 375 or 1000 mg/$m^2$ subject surface area.

The desired dose may be delivered once or several times daily, weekly, bi-weekly, thrice weekly, monthly, bi-monthly, thrice-monthly, or at any other frequency that has therapeutic benefit, as determined by the health professional supervising the administration.

In some embodiments of the present invention, the dosing regimen includes administering the desired dose for a total of 2, 3, 4, 5, 6, 7, 8, 9, 10, 11, 12, 13, 14, 15, 16, 17, 18, 19, 20, 21, 22, 23, 24, 25, 26, 27, 28, 29, or 30 times. In some embodiments of the present invention, the doses are administered in one cycle. In some embodiments of the present invention, the doses are administered in 2, 3, 4, 5, 6, 7, 8, 9, or 10 cycles.

In a preferred embodiment, rituximab is administered to a subject at a dose of 375 mg/m$^2$ once per week for three weeks.

In some embodiments of the present invention, the therapeutic agent that destroys B lymphocytes in accordance with the present invention is administered in accordance with the dosage forms approved by the FDA for this type of product.

Treatment of IDDM

The present invention provides a method of treating insulin-dependent diabetes mellitus in a subject including administering to the subject a therapeutically effective amount of a Janus kinase inhibitor, or a pharmaceutically acceptable salt or ester thereof, therapeutically effective amount of intravenous immunoglobulin, or therapeutically effective amount of a therapeutic agent that destroys B lymphocytes, or combinations thereof. In some embodiments of the present invention, the Janus kinase inhibitor, or a pharmaceutically acceptable salt or ester thereof, is a JAK1/3 inhibitor or JAK3 inhibitor. In some embodiments of the present invention, the Janus kinase inhibitor, or a pharmaceutically acceptable salt or ester thereof, is a JAK1/3 inhibitor. In some embodiments of the present invention, the Janus kinase inhibitor, or a pharmaceutically acceptable salt or ester thereof, is tofacitinib. In a preferred embodiment of the present invention, the Janus kinase inhibitor, or a pharmaceutically acceptable salt thereof, is tofacitinib citrate. In some embodiments of the present invention, the therapeutic agent that destroys B lymphocytes (B cells) is an anti-CD20 antibody agent. In a preferred embodiment of the present invention, the therapeutic agent that destroys B lymphocytes (B cells) is the antibody rituximab, or fragments thereof.

In some embodiments of the present invention, the subject that is treated is in need of such treatment. A subject in need of treatment may include individuals already having a specified condition or disorder (e.g., IDDM), individuals who are at risk for developing or acquiring that condition or disorder (e.g., IDDM), and/or individuals in which the condition or disorder is to be prevented or treated. Treatment thus includes therapeutic as well as prophylactic/preventative measures.

In accordance with the present invention, the JAK inhibitor, or a pharmaceutically acceptable salt or ester thereof, intravenous immunoglobulin and anti-CD20 antibody agent may be administered according to any therapeutically appropriate route and dosing regimen, including those disclosed elsewhere herein.

In a preferred embodiment of the present invention, the JAK inhibitor, or a pharmaceutically acceptable salt or ester thereof, is administered orally, and the intravenous immunoglobulin and anti-CD20 antibody agent are administered intravenously by infusion.

In some embodiments of the present invention, the exact dosing regimen may vary from subject to subject, depending on one or more factors as is well known in the medical arts. Such factors may include, for example, one or more of the following: the subject's age, body weight, general health, sex, diet and general condition; the severity of the infection; the specific pharmaceutical composition administered and its half-life; the route of administration; the pharmacokinetics and pharmacodynamics of the active pharmaceutical ingredient; the disorder being treated and the severity of the disorder; the activity of the specific antibody agent employed; the duration of the treatment; other active pharmaceutical ingredients used in combination or coincidental with the specific compound employed and the like. Pharmaceutical compositions may be formulated such that the dosage unit is equivalent to the dose amount for ease of administration and uniformity of dosing. It will be understood, however, that the total daily, weekly or monthly usage of the pharmaceutical compositions and dosage forms of the present invention will be decided by the attending physician within the scope of sound medical judgment.

In a preferred embodiment of the present invention, the dosing regimens and routes of the administration of the JAK inhibitor, or pharmaceutically acceptable salt or ester thereof, intravenous immunoglobulin and therapeutic agent that destroys B lymphocytes are those approved by the FDA.

In some embodiments of the present invention, tofacitinib citrate is administered as an immediate-release tablet including about 8 mg of tofacitinib citrate (corresponding to about 5 mg of tofacitinib free base) and excipients, such as but not limited to one or more binders, or one or more diluents, or one or more disintegrants, or one or more lubricants, or combinations thereof.

In some embodiments of the present invention, tofacitinib citrate is administered as an extended release tablet including about 17.77 mg of tofacitinib citrate (corresponding to about 11 mg of tofacitinib free base) and excipients, such as but not limited to one or more binders, or one or more diluents, or one or more disintegrants, or one or more lubricants, or combinations thereof.

In some embodiments of the present invention, tofacitinib citrate is administered as an immediate-release tablet including the following excipients: microcrystalline cellulose, lactose monohydrate, croscarmellose sodium, magnesium stearate, HPMC 2910/Hypromellose 6 cP, titanium dioxide, macrogol/PEG3350, and triacetin.

In some embodiments of the present invention, tofacitinib citrate is administered as an extended release tablet including the following excipients: sorbitol, hydroxyethyl cellulose, copovidone, magnesium stearate, cellulose acetate, hydroxypropyl cellulose, HPMC 2910/Hypromellose, titanium dioxide, triacetin, and red iron oxide. Printing ink contains shellac glaze, ammonium hydroxide, propylene glycol, and ferrosoferric oxide/black iron oxide.

In some embodiments of the present invention, tofacitinib citrate is administered once, twice or thrice daily; once, twice or thrice weekly; or once, twice or thrice monthly; at a dose of 1, 2, 3, 4, 5, 6, 7, 8, 9, 10, 11, 12, 13, 14, 15, 16, 17, 17.77, 18, 19, 20, 21, 22, 23, 24, 25, 27, 28, 29, or 30 mg per dosage unit administered.

In preferred embodiments, 8 or 16 mg of tofacitinib citrate is administered to the patient once or twice daily.

In some embodiments of the present invention, the dose of intravenous immunoglobulin for patients with IDDM is about 0.01, about 0.1, about 1, about 2, about, 3, about, 4, about 5, about 10, about 50 or about 100 mg/kg body weight of the patient.

In some embodiments of the present invention, a dose of intravenous immunoglobulin is administered once daily; or once every 2, 3, 4, 5, 6 or 7 days; or once every week; or once every 2, 3, 4, 5, 6, 7, 8, 9 or 10 weeks, for a total 1, 2, 3, 4, 5, 6, 7, 8, 9, or 10 doses.

In some embodiments of the present invention, a dose of intravenous immunoglobulin is administered at the beginning of the dosing regimen on several consecutive days (e.g., 2, 3, 4, 5, 6, 7, 8, 9 or 10 days), and then administered every 1, 2, 3, 4, 5, 6, 7, 8, 9, or 10 weeks. In a preferred embodiment of the present invention, a dose of intravenous immunoglobulin is administered on each of days 1, 2 and 3 at the beginning of the dosing regimen. In a preferred embodiment of the present invention, doses of intravenous immunoglobulin are administered every 3 weeks after the administration of doses of intravenous immunoglobulin on 3 consecutive days at the beginning of the dosing regimen. In a preferred embodiment of the present invention, these first three doses are 1 or 2 mg intravenous immunoglobulin.

In a preferred embodiment, two immediate-release tablets each comprising 8 mg of tofacitinib citrate and the excipients microcrystalline cellulose, lactose monohydrate, croscarmellose sodium, magnesium stearate, HPMC 2910/Hypromellose 6 cP, titanium dioxide, macrogol/PEG3350, and triacetin are administered to the subject twice daily, and 1 to 2 mg intravenous immunoglobulin per kg weight of the subject is administered every 1 to 3 weeks, after an initial loading dose of 2 mg/Kg of IVIG on the first day followed by doses of 1 mg/Kg IVIG on the second and third day.

In some embodiments of the present invention, rituximab is administered as an infusion at a dose of from 100 to 1000 mg/m$^2$ once or several times daily, weekly, bi-weekly, thrice weekly, monthly, bi-monthly, thrice-monthly, or at any other frequency that has therapeutic benefit, as determined by the health professional supervising the administration.

In a preferred embodiment, rituximab is administered to a subject at a dose of 375 mg/m$^2$ once per week for three weeks.

The therapeutically effective amounts of the JAK inhibitor, or pharmaceutically acceptable salt or ester thereof, intravenous immunoglobulin and therapeutic agent that destroys B lymphocytes are determined by the person skilled in the art (e.g., physician) in accordance with the definitions provided herein and in accordance with common knowledge in the art. In preferred embodiments, these therapeutically effective amounts are determined based on the measurements and IDDM biomarkers disclosed in the Examples (e.g., insulin, insulin auto-Abs, pancreatic auto-Abs).

In accordance with the definitions provided herein, the JAK inhibitor, or pharmaceutically acceptable salt or ester thereof, and the intravenous immunoglobulin; the JAK inhibitor, or pharmaceutically acceptable salt or ester thereof, and the therapeutic agent that destroys B lymphocytes; the intravenous immunoglobulin and the therapeutic agent that destroys B lymphocytes; or the JAK inhibitor, or pharmaceutically acceptable salt or ester thereof, the intravenous immunoglobulin and the therapeutic agent that destroys B lymphocytes may be administered in combination with each other, i.e., as a combination therapy. These therapeutic agents may be administered concurrently with, prior to, or subsequent to, one another. It will be appreciated that therapeutic agents utilized in combination may be administered together in a single composition or dosage unit or administered separately in different compositions or dosage units. In general, each therapeutic agent will be administered at a dose and/or with a dosing regimen optimized for that particular therapeutic agent.

Also within the scope of the present invention are therapeutic regimens that include not only one or more of a therapeutically effective amount of a Janus kinase inhibitor, or a pharmaceutically acceptable salt or ester thereof, a therapeutically effective amount of intravenous immunoglobulin, and/or a therapeutically effective amount of a therapeutic agent that destroys B lymphocytes, but additionally one or more therapeutic agents. These additional therapeutic agents may be an additional Janus kinase inhibitor, or pharmaceutically acceptable salt or ester thereof, intravenous immunoglobulin, and/or therapeutic agent that destroys B lymphocytes. These additional therapeutic agents may also be therapeutic agents that are not a Janus kinase inhibitor, or pharmaceutically acceptable salt or ester thereof, intravenous immunoglobulin, or therapeutic agent that destroys B lymphocytes. In one embodiment of the present invention, these additional therapeutic agents may be therapeutic agents that are commonly used to treat IDDM, for example insulin. In one embodiment of the present invention, administration of insulin to a subject, or treatment of the subject with insulin, starts before the point in time when one or more of tofacitinib, IVIG and rituximab are administered to the subject, or when the subject is treated with one or more of tofacitinib, IVIG and rituximab, and continues even after this point in time. In one embodiment of the present invention, administration of insulin to a subject, or treatment of the subject with insulin, continues, or starts, when administration of, or treatment with, one or more of tofacitinib, WIG and rituximab ceases.

In some embodiments of the present invention, the term "pharmaceutically acceptable" as used herein refers to agents that, within the scope of the sound medical judgment of the person having ordinary skill in the art, are suitable for use in contact with tissues of animals (e.g., humans) without excessive toxicity, irritation, allergic response, or other problems or complications, commensurate with a reasonable benefit/risk ratio.

In some embodiments of the present invention, the term "pharmaceutically acceptable carrier" as used herein refers to a pharmaceutically acceptable material, composition or vehicle, such as a liquid or solid filler, diluent, or solvent that is part of a pharmaceutical composition or dosage form containing a therapeutic agent. Some examples of materials which can serve as pharmaceutically acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; materials such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters; polycarbonates and/or polyanhydrides; and other non-toxic compatible substances commonly employed in pharmaceutical formulations. As used herein, the terms carrier and excipient have the same meaning and are used interchangeably.

In some embodiments of the present invention, the term "pharmaceutically acceptable salt(s)" refers to acid addition salts that retain the biological effectiveness of the free bases and that are not biologically or otherwise undesirable. The manufacture, selection and use of such acid addition salts is generally known by the person having ordinary skill in the art. Such pharmaceutically acceptable acid addition salts may be formed with a number of different acids, which include, but are not limited to, inorganic acids such as hydrochloric acid, hydrobromic acid, sulfuric acid, nitric acid, phosphoric acid, and the like, as well as organic acids such as acetic acid, trifluoroacetic acid, propionic acid, hexanoic acid, heptanoic acid, cyclopentanepropionic acid, glycolic acid, pyruvic acid, lactic acid, malic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, stearic acid, and the like.

In some embodiments of the present invention, the term "pharmaceutically acceptable salt(s)" also refers to base addition salts that are not biologically or otherwise undesirable. The manufacture, selection and use of such base addition salts is generally known by the person having ordinary skill in the art. Such pharmaceutically acceptable base addition salts may be for example, but are not limited to, metallic salts made from aluminum, calcium, lithium, magnesium, potassium, sodium and zinc, or organic salts made from lysine, N,N'-dibenzylethylenediamine, chloroprocaine, choline, diethanolamine, ethylenediamine, meglumine (N-methylglucamine) and procaine. See, e.g., Remington's Pharmaceutical Sciences, 18th eds., Mack Publishing, Easton Pa. (1990) or Remington: The Science and Practice of Pharmacy, 19th eds., Mack Publishing, Easton Pa. (1995).

The contents of all documents (scientific articles, patents, published patent applications or other documents) cited herein are incorporated herein by reference in their entirety.

The invention will be more fully understood by reference to the following Examples. They should not, however, be construed as limiting the scope of the invention.

EXAMPLES

Example 1

A 14 years old male patient diagnosed with IDDM was treated with 8 units of exogenous long-acting insulin per day (administered in the evening) and 1 unit of short-acting insulin per 6 grams of carbohydrate food intake (administered before each meal).

The patient was then treated twice-daily with a 5 mg dose of tofacitinib (calculated based on the weight of tofacitinib free base; corresponding to 8 mg of tofacitinib citrate) for a period of six months, using one tablet of the Xeljanz® immediate-release tofacitinib citrate tablet drug product twice-daily (BID). Starting three days post initiation of tofacitinib treatment, the patient did not receive any short-acting insulin and was kept solely on long-acting insulin (8 units per day, administered in the evening). Starting three weeks post initiation of tofacitinib treatment, the patient did not receive any exogenous insulin.

About six months post initiation of tofacitinib treatment, the tofacitinib dosing regimen was increased to 10 mg tofacitinib twice daily (calculated based on the weight of tofacitinib free base; corresponding to 16 mg of tofacitinib citrate), using two tablets of the Xeljanz® immediate-release tofacitinib citrate tablet drug product twice-daily (BID). Specific stimulation high-carb diet was introduced occasionally to monitor the patient's pancreatic ability to respond to the glycemic demands.

At about 10 months post initiation of tofacitinib treatment, the patient had gained overall weight and muscle mass. Since the patient's sugar levels fluctuated and no further change of his auto-antibody blood titers was detected at this point (see Table 1 below), the patient was additionally treated with intravenous immunoglobulin (WIG) (Gamunex®-C immunoglobulin product from Grifols Therapeutics Inc.) at the dosages and time points indicated in Tables 1-2 to further improve the patient's condition. Each IVIG dose was administered in one continuous infusion session. From week 16 to week 42, the patient was also treated with alpha one antitrypsin.

Throughout the patient's treatment, the patient's blood was drawn at the time points indicated in Tables 1-2 below, and analyzed by established testing laboratories with respect to standard IDDM blood parameters (see Tables 1-2, top row of each table listing the markers assayed; the numerical values in parenthesis after some of the markers indicate normal reference levels).

As can be seen, tofacitinib treatment and IVIG treatment had a synergistic effect. In particular, the data in Table 1 show a reduction in pancreatic islet-cell auto-antibodies and anti-insulin auto-antibodies upon treatment with tofacitinib. A further reduction can be seen upon additional treatment with IVIG (see data points in left-most two data-columns in Table 1).

Additionally, addition of anti-CD20 antibody agent "Rituxan", given intravenously to the patient showed a synergistic effect with the tofacitinib treatment and IVIG treatment. Rituxan and IVIG administration was carried out according to the published regimen (Ahmed et al. New England Journal of Medicine 355:17 (2006)). The patient was dosed at 750 mg intravenously on weeks 87, 88, 89 and 90. Comparing the pancreatic islet-cell auto-antibodies and anti-insulin auto-antibodies upon treatment with tofacitinib in week 82.5 to the pancreatic islet-cell auto-antibodies and anti-insulin auto-antibodies upon treatment with tofacitinib with rituxan and IVIG in week 87.5, a significant reduction can be seen.

The "date" columns in Tables 1-2 indicate the weeks post-tofacitinib treatment initiation that further treatment was administered to the patient, and the points in time when the patient's bloodwork was done. The patient's 8 mg tofacitinib citrate BID treatment regimen (as described) started in week zero and ended 25 weeks later (see Tables 1-2). The patient's 16 mg tofacitinib citrate BID treatment regimen (as described) started in week 25 and is still ongoing with an exception in weeks 77-79 (see Tables 1-2). Tables 1 and 2 describe the same treatment but include data points with respect to different markers tested.

TABLE 1

| | treatment | | data points | | | |
|---|---|---|---|---|---|---|
| date | tofacitinib citrate | IVIG | Insulin Auto Ab (<0.4) | IA2 Ab (Islet cell Ab Screen) (<0.8) | Islet Cell Ab Titers | Glucose |
| week −3 | — | — | 6.8 | — | 80 | 519 |
| week −0.5 | — | — | 47 | 160 | — | — |
| week 0 | 8 mg BID | — | — | — | — | — |
| week 4 | | — | 7.2 | 43.8 | — | — |
| week 9 | | — | — | — | — | — |

TABLE 1-continued

| | treatment | | data points | | | |
|---|---|---|---|---|---|---|
| date | tofacitinib citrate | IVIG | Insulin Auto Ab (<0.4) | IA2 Ab (Islet cell Ab Screen) (<0.8) | Islet Cell Ab Titers | Glucose |
| week 10 | — | — | 64 | >50 | — | — |
| week 13 | — | — | 6.1 | 46.2 | 320 | 104 |
| week 19 | — | — | 6.6 | 37.7 | 80 | 126 |
| week 22 | — | — | 4 | — | negative | 210 |
| week 25 | — | — | 5.3 | — | 20 | — |
| week 25.5 | — | — | — | — | — | — |
| week 26 | — | — | 5 | 47.3 | negative | 93 |
| week 29 | — | — | 4.6 | 47.7 | 20 | 85 |
| week 30 | — | — | 4.2 | 43.8 | — | 143 |
| week 36 | — | — | 2.4 | 46.5 | 20 | — |
| week 44 (day 1) | 16 mg BID | 2 mg/Kg = 150 mg total infusion of IVIG | — | — | — | — |
| week 44 (day 2) | | 1 mg/Kg = 75 mg total infusion of IVIG | | | | |
| week 44 (day 3) | | 1 mg/Kg = 75 mg total infusion of IVIG | | | | |
| week 47 | | — | 2.1 | 17 | negative | — |
| week 47.5 | | 1 mg/Kg = 75 mg total infusion of IVIG | | | | |
| week 50 | | — | 0.9 | 35.7 | negative | — |
| week 50.5 | | 1 mg/Kg = 75 mg total infusion of IVIG | | | | |
| week 53 | | — | 0.8 | 30 | negative | 97 |
| week 54 | | 1 mg/Kg = 75 mg total infusion of IVIG | | | | |
| week 57 | | — | 1 | 25.9 | negative | 168 |
| week 61 | | — | 0.9 | 39.4 | negative | 160 |
| week 66 | | — | 0.9 | 38.8 | negative | — |
| week 70 | | — | 1.7 | 39.4 | negative | 112 |
| week 75 | | — | 0.7 | 39.2 | negative | 113 |
| week 77 | 5 mg QAM & 10 mg QHS | — | — | — | — | — |
| week 79 | | — | 0.5 | 44.5 | negative | 85 |
| week 82 | 10 mg BID | — | — | — | — | — |
| week 82.5 | | — | 0.5 | 46 | negative | 230 |
| week 86 | | 2 gm/Kg | — | — | — | — |
| week 86.15 | | 1 gm/Kg | | | | |
| week 86.30 | | 1 gm/Kg | | | | |
| week 87.5 | | — | <0.4 | 6.5 | negative | 278 |
| week 89 | | 1 gm/Kg | — | — | — | — |
| week 91.25 | | — | <0.4 | 13.1 | negative | 148 |
| week 92.25 | | — | 0.5 | 25.6 | negative | 148 |
| week 99.25 | | — | 0.7 | 26.5 | 20 | 170 |

TABLE 2

| | treatment | | data points | | | | |
|---|---|---|---|---|---|---|---|
| date | tofacitinib citrate | IVIG | C-Peptide (0.8-3.85) | Insulin (2-19.6) | HgbA1C | GAD-65 (<5) | Tyrosine (31-108) |
| week −3 | — | — | 0.6 | 3.8 | 13.6 | — | — |
| week −0.5 | — | — | 1.08 | 27 | — | <5 | 116 |
| week 0 | 8 mg BID | — | — | — | — | — | — |
| week 4 | | — | 2.66 | 17.1 | — | — | 79 |
| week 9 | | — | 1.5 | 7.8 | 7.2 | — | 90 |
| week 10 | | — | 4.7 | 34.5 | — | — | — |
| week 13 | | — | 1.43 | — | — | — | 74 |
| week 19 | | — | 1.79 | 12 | 6.1 | <5 | 83 |
| week 22 | | — | — | 24.8 | 6.1 | — | — |
| week 25 | | — | — | — | — | — | — |
| week 25.5 | 16 mg BID | — | — | — | — | — | — |
| week 26 | | — | 2.19 | 12 | — | <5 | 91 |
| week 29 | | — | 1.34 | 5.4 | 6.2 | — | — |

TABLE 2-continued

| date | treatment | | data points | | | | |
| --- | --- | --- | --- | --- | --- | --- | --- |
| | tofacitinib citrate | IVIG | C-Peptide (0.8-3.85) | Insulin (2-19.6) | HgbA1C | GAD-65 (<5) | Tyrosine (31-108) |
| week 30 | | — | 2.74 | 34.3 | 6.3 | <5 | — |
| week 36 | | — | 3.17 | 31.1 | — | — | — |
| week 44 (day 1) | | 2 mg/Kg | — | — | — | — | — |
| week 44 (day 2) | | 1 mg/Kg | — | — | — | — | — |
| week 44 (day 3) | | 1 mg/Kg | — | — | — | — | — |
| week 47 | | — | — | — | 6.9 | — | — |
| week 47.5 | | 1 mg/Kg = 75 mg total infusion of IVIG | — | — | — | — | — |
| week 50 | | — | 2.73 | 25 | 6.5 | — | — |
| week 50.5 | | 1 mg/Kg = 75 mg total infusion of IVIG | — | — | — | — | — |
| week 53 | | | 2.14 | 14.8 | 6.5 | 66 | 75 |
| week 54 | | 1 mg/Kg = 75 mg total infusion of IVIG | — | — | — | — | — |
| week 57 | | — | 5.21 | 47.3 | 6.8 | 70 | 105 |
| week 61 | | — | 4.3 | 37.2 | 6.2 | 15 | — |
| week 66 | | — | 1.38 | 7.7 | 6.5 | 7 | — |
| week 70 | | — | 1.22 | 6.4 | 6.3 | <5 | — |
| week 75 | | — | 1.33 | 6.6 | 6.2 | <5 | — |
| week 79 | | — | 1.61 | 5.6 | 6.4 | <5 | — |
| week 77 | 5 mg | — | — | — | — | — | — |
| week 79 | QAM & 10 mg QHS | — | 1.61 | 5.6 | 6.4 | <5 | — |
| week 82 | 10 mg BID | — | — | — | — | — | — |
| week 82.5 | | — | 2.81 | 24.1 | 6.9 | <5 | — |
| week 86 | | 2 gm/Kg | — | — | — | — | — |
| week 86.15 | | 1 gm/Kg | — | — | — | — | — |
| week 86.30 | | 1 gm/Kg | — | — | — | — | — |
| week 87.5 | | — | 1.68 | 6.1 | 8.1 | 105 | — |
| week 89 | | 1 gm/Kg | — | — | — | — | — |
| week 91.25 | | — | 2.88 | 47.8 | 7.8 | 131 | — |
| week 92.25 | | — | 2.36 | 33.7 | 7.1 | 48 | — |
| week 99.25 | | — | 1.41 | 14.3 | 6.9 | 24 | — |

Example 2

A patient (appr. 60 kg) diagnosed with IDDM is treated with a combination of tofacitinib and IVIG at the following doses for a period of three months:

(1) 16 mg tofacitinib citrate twice-daily (equivalent to 10 mg tofacitinib free base), using the Xeljanz® immediate-release tofacitinib citrate tablet drug product from Pfizer (each tablet including 8 mg of tofacitinib citrate, equivalent to 5 mg tofacitinib free base); and (2) a loading dose of 2 mg IVIG/Kg subject body weight on the first day of treatment followed by doses of 1 mg IVIG/Kg on the second and third day. This is followed by maintenance doses of 1 mg IVIG/Kg every three weeks. The Gamunex®-C immunoglobulin product from Grifols Therapeutics Inc. is used.

Three months after treatment initiation, the patient is treated for another three weeks with a combination tofacitinib/IVIG as before and additionally 375 mg/m² rituximab once per week for three weeks.

Afterwards, rituximab is discontinued and the IVIG is continued at the same dose (i.e., maintenance doses of 1 mg/Kg every three weeks) for another two months, and then discontinued. Tofacitinib is continued at the same dose (i.e., 16 mg BID (equivalent to 10 mg tofacitinib free base)).

Once the patient's blood glucose levels and blood levels of insulin and pancreatic and insulin autoantibodies return to normal, tofacitinib doses are gradually reduced. Tofacitinib treatment is then either discontinued in case there is no need for further treatment, or maintained at the lowest level that can control the patient's glucose levels. Blood tests are performed once every three months over a period of two years to assure that the patient's glucose levels and levels of insulin and pancreatic and insulin autoantibodies remain normal.

In parallel to the aforesaid therapeutic regimen, the patient may also receive exogenous insulin. Exogenous insulin may also be administered after the administration of one or more of tofacitinib, IVIG and rituximab has been discontinued.

Example 3

A patient is treated for IDDM with tofacitinib. The patient also receives IVIG for the treatment of IDDM. On the first three days of treatment with IVIG, 2, 1 and 1 mg IVIG/Kg subject body weight are administered, respectively. Then, the patient receives 1 mg IVIG/Kg subject body weight three weeks after the aforesaid dose on day three, and another 1 mg IVIG/Kg subject body weight dose three weeks later. One day after the last IVIG dose, the patient receives a dose of rituximab and then two more rituximab doses at one week intervals. Right after the third rituximab dose, the patient receives another 1 mg IVIG/Kg subject body weight dose, and then a last 1 mg IVIG/Kg subject body weight dose three weeks later. The patient continues to receive tofacitinib.

What is claimed is:

1. A method of treating insulin-dependent diabetes mellitus in a subject, comprising administering to the subject tofacitinib citrate; and administering to the subject intravenous immunoglobulin; and administering to the subject rituximab.

2. The method of claim 1, wherein the tofacitinib citrate is administered at a dose from 4 mg to 64 mg per day; and wherein the intravenous immunoglobulin is administered at a dose of from 0.2 mg to 100 mg per kg weight of the subject every 1 to 4 weeks; and wherein the rituximab is administered at a dose of from 50 mg/m$^2$ to 700 mg/m$^2$ surface of the subject every 1 to 4 weeks.

3. The method of claim 2, wherein the tofacitinib citrate is administered as immediate-release tablet or extended-release tablet comprising from 2 mg to 30 mg tofacitinib citrate; and wherein the intravenous immunoglobulin is administered as a sterile solution for injection comprising from 2%-50% protein; and wherein the rituximab is administered intravenously at a concentration of 0.2 mg/mL to 20 mg/mL.

4. The method of claim 3, wherein the tofacitinib citrate is administered at a dose from about 8 mg to about 32 mg per day as an immediate-release tablet comprising about 8 mg tofacitinib citrate or as an extended-release tablet comprising about 17.77 mg tofacitinib citrate or both; and wherein the intravenous immunoglobulin is administered as a sterile solution for injection comprising from 5%-20% protein at a dose of from 1 mg to 2 mg per kg weight of the subject every 1 to 4 weeks; and wherein the rituximab is administered intravenously at a concentration of 1 mg/mL to 4 mg/mL at a dose of 375 mg/m$^2$ surface of the subject once per week.

5. The method of claim 4, wherein the tofacitinib citrate is administered at a dose of 32 mg per day as an immediate-release tablet comprising about 8 mg tofacitinib citrate; and
wherein the intravenous immunoglobulin is administered at a dose of 1 mg per kg weight of the subject every 3 weeks for a total of 5 to 6 months, and wherein intravenous immunoglobulin is administered at a dose of 2 mg per kg weight of the subject on a first day of treatment followed by doses of 1 mg per kg weight of the subject on second and third days of treatment; and wherein the rituximab is administered for a period of three weeks.

6. A method of treating insulin-dependent diabetes mellitus in a subject, comprising administering to the subject tofacitinib citrate; and administering to the subject intravenous immunoglobulin, and optionally a therapeutically effective amount of a therapeutic agent that destroys B lymphocytes.

7. The method of claim 6, wherein the tofacitinib citrate is administered at a dose from 4 mg to 64 mg per day; and wherein the intravenous immunoglobulin is administered at a dose of from 0.2 mg to 100 mg per kg weight of the subject every 1 to 4 weeks.

8. The method of claim 7, wherein the tofacitinib citrate is administered as immediate-release tablet or extended-release tablet comprising from 2 mg to 30 mg tofacitinib citrate; and wherein the intravenous immunoglobulin is administered as a sterile solution for injection comprising from 2%-50% protein.

9. The method of claim 8, wherein the tofacitinib citrate is administered at a dose from about 8 mg to about 32 mg per day as an immediate-release tablet comprising about 8 mg tofacitinib citrate or as an extended-release tablet comprising about 17.77 mg tofacitinib citrate or both; and wherein the intravenous immunoglobulin is administered as a sterile solution for injection comprising from 5%-20% protein at a dose of from 1 mg to 2 mg per kg weight of the subject every 1 to 4 weeks.

10. The method of claim 9, wherein the tofacitinib citrate is administered at a dose of 32 mg per day as an immediate-release tablet comprising about 8 mg tofacitinib citrate; and
wherein the intravenous immunoglobulin is administered at a dose of 1 mg per kg weight of the subject every 3 weeks for a total of 5 to 6 months, and wherein intravenous immunoglobulin is administered at a dose of 2 mg per kg weight of the subject on a first day of treatment followed by doses of 1 mg per kg weight of the subject on second and third days of treatment.

11. The method of claim 6, wherein therapeutically effective amounts of tofacitinib citrate, and intravenous immunoglobulin, and rituximab are administered.

12. The method of claim 6, wherein therapeutically effective amounts of tofacitinib citrate and intravenous immunoglobulin, are administered.

13. The method of claim 6, wherein the subject is in need of treatment.

14. The method of claim 6, wherein the antibody agent is an anti-CD20 antibody agent.

15. The method of claim 14, wherein the anti-CD20 antibody agent comprises amino acid sequences substantially identical to the CDRs of rituximab.

* * * * *